United States Patent [19]

Hamilton et al.

[11] Patent Number: 5,783,408

[45] Date of Patent: Jul. 21, 1998

[54] METHOD FOR SCREENING POTENTIAL ANTI-OBESITY AGENTS

[76] Inventors: Bradford S. Hamilton, D7 - 245 Howland Avenue, Toronto, Ontario, Canada, M5R 3B7; Daniel A. K. Roncari, deceased, late of North York, Canada; by Lubov Roncari, executor, 144 Esther Crescent, Thornhill, Ontario, Canada, L4J 3L4

[21] Appl. No.: 487,424

[22] Filed: Jun. 7, 1995

[51] Int. Cl.[6] .................... C12Q 1/02; C12Q 1/00; G01N 31/00; C07D 239/00

[52] U.S. Cl. .................... 435/29; 435/4; 436/13; 436/71; 436/106; 544/242; 544/267; 514/263; 536/6.2; 536/4.1; 536/1.11; 424/574; 424/442

[58] Field of Search .................... 435/29, 4; 436/13, 436/71, 106; 544/242, 267; 514/263; 536/6.2, 4.1, 1.11; 424/574, 442

[56] References Cited

U.S. PATENT DOCUMENTS

| | | | |
|---|---|---|---|
| 3,852,451 | 12/1974 | Cunningham | 424/574 |
| 3,864,469 | 2/1975 | Reisner | 544/242 |
| 5,256,398 | 10/1993 | McAfee et al. | 514/263 |
| 5,268,295 | 12/1993 | Serrero | 435/29 |
| 5,288,721 | 2/1994 | Klein et al. | 514/263 |
| 5,300,298 | 4/1994 | LaNoue | 514/263 |
| 5,449,757 | 9/1995 | Serrero | 530/350 |

FOREIGN PATENT DOCUMENTS

| | | |
|---|---|---|
| 0 063 827 | 11/1982 | European Pat. Off. |
| WO 93/21783 | 11/1993 | WIPO |
| WO 94/02150 | 2/1994 | WIPO |
| WO 95/18533 | 7/1995 | WIPO |
| WO 96/40226 | 12/1996 | WIPO |

Primary Examiner—Louise Leary
Attorney, Agent, or Firm—Foley & Lardner

[57] ABSTRACT

A method for screening a compound as a potential anti-obesity agent by determining whether the compound stimulates micro motion of cells in vitro is described 9 Claims, 12 Drawing Sheets

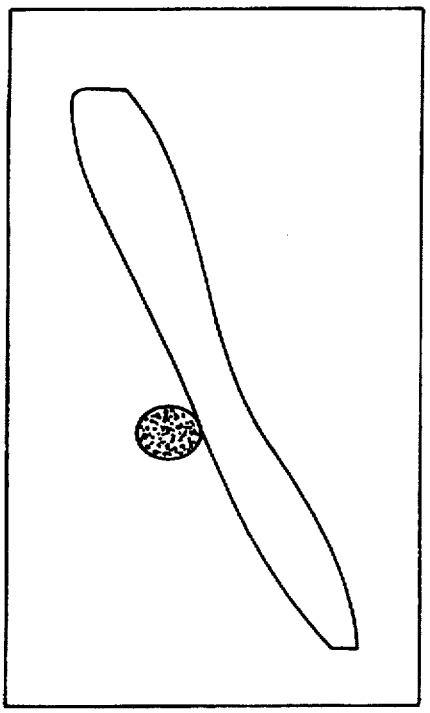
FIG. 4(b)
TIME 2
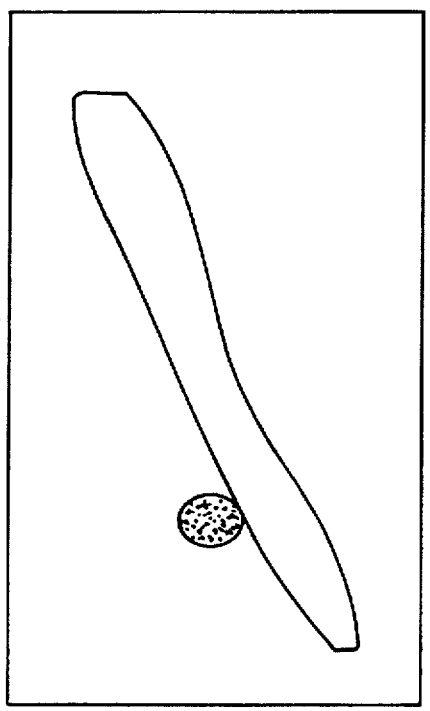
FIG. 4(a)
TIME 1
Σ PIXEL VALUES = RELATIVE MOTION
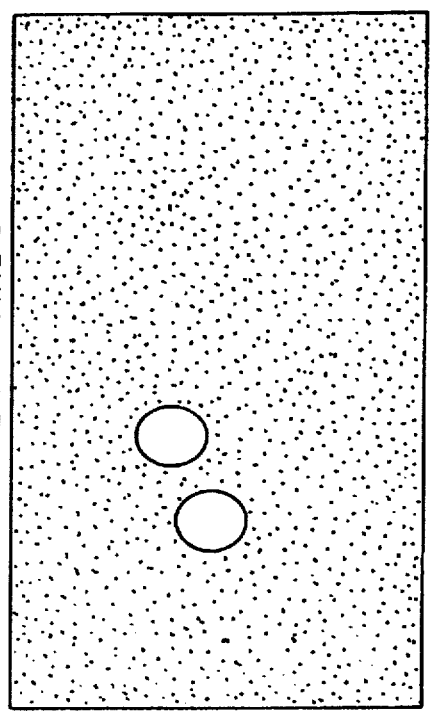
FIG. 4(c)
TIME 1 − TIME 2

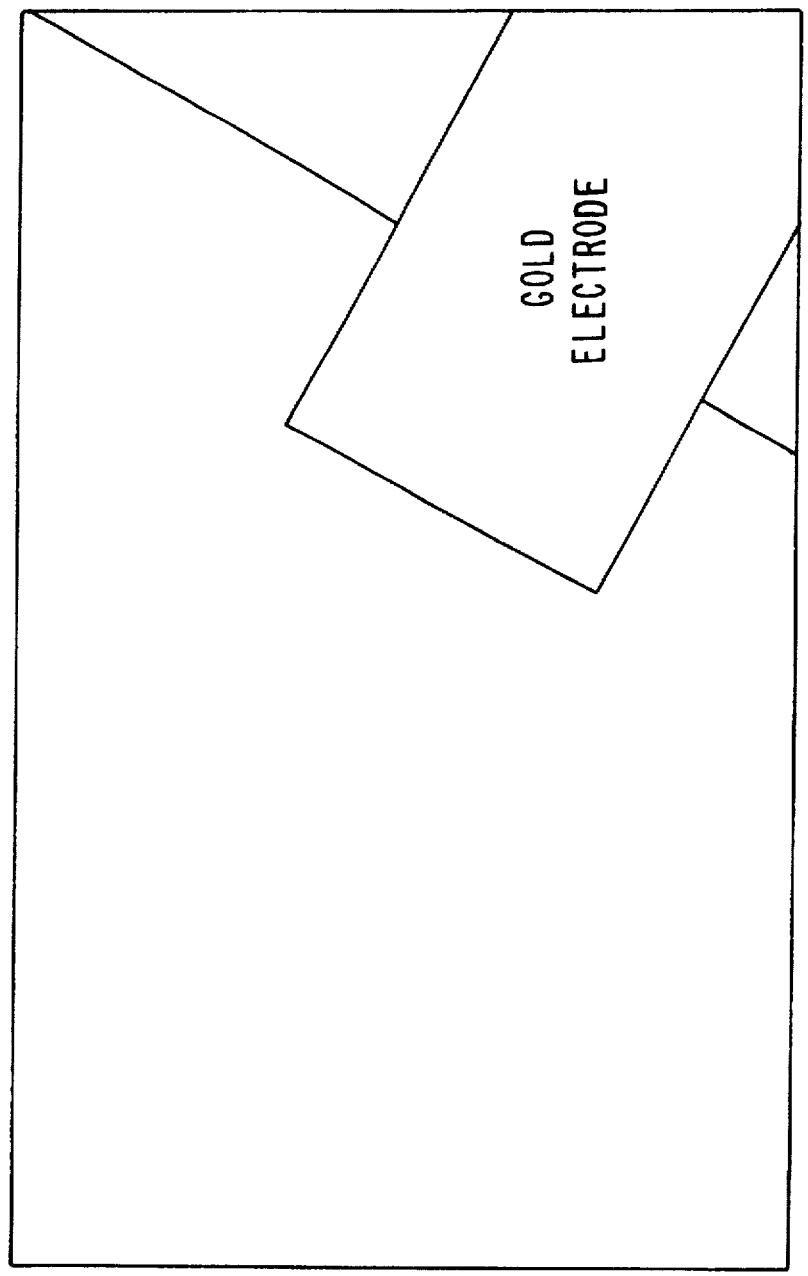

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:1:

GCGCGTTCCC TGCAAGACTG AG 22

( 2 ) INFORMATION FOR SEQ ID NO:2:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:2:

GTTTGTCCAT ATGCAAATAT TGTTCC 26

METHOD FOR SCREENING POTENTIAL ANTI-OBESITY AGENTS

The present invention relates to a method for screening compounds having potential as anti-obesity agents.

Obesity is a significant health problem in many countries and has been extensively reviewed in the literature.[1,2,3,4,5,6] Obesity is frequently associated with such cardiovascular risk factors as dyslipidemias (particularly, elevated levels of very-low-density lipoprotein-triglycerides and depressed levels of high-density lipoproteins), hypertension, hyperinsulinemia, and non-insulin dependent diabetes mellitus.[1,2,3,4,5,6] Massive corpulence (body weight greater than 170% of reference or body mass index greater than 37 kg/m$^2$) is also characterized by high morbidity and mortality.[1,2,6] Massive obesity, which features diffuse distribution of adiposity, is particularly associated with the mixed (central and obstructive) sleep-apnea syndrome, and at times the full hypoventilation syndrome, gallbladder disease, non-insulin dependent diabetes, trauma and psychosocial problems.

It has been estimated that approximately 34 million American adults were obese in 1980.[7] The economic costs in 1986 of obesity were estimated conservatively to be $39.3 billion.

Billions of dollars have been allocated to research aimed at unravelling causes of obesity. Much of the research has been in the field of adipose tissue and fat cells, as well as adaptive thermogenesis and brown adipose tissue. It is fair to say that, despite prodigious amounts of research for several decades, the etiology for the striking variations between individuals in vulnerability to obesity remains unclear.

It has been postulated that a reciprocal relationship exists between energy utilization for cellular "biomechanical-molecular mobility" processes and body fat content.[8] According to the hypothesis, which is only briefly described here, after utilization for indispensable metabolic needs and the variable "biomechanical-mobile" activity, excess energy is mainly transduced to anabolic processes, and eventually stored as chemical energy, mostly as adipocyte triglycerides.

"Biomechanical-mobile" activity is a collective term adopted herein to include cellular biomechanical functions mediated by the cytoskeleton. After energy utilization for life-sustaining processes such as maintenance of electrochemical gradients across membranes, a significant portion of the extra energy that is not consumed by biomechanical processes is converted to chemical energy storage. It is postulated that differences in energy consumed by biomechanical processes are thus associated with differences between individuals in the amount of energy that is ultimately stored as triglycerides. In other words, a greater amount of energy consumed by biomechanical processes will lead to a lower amount of energy ultimately stored as triglycerides. Conversely, a lower amount of energy consumed by biomechanical processes will lead to a higher amount of energy ultimately stored as triglycerides.

Consistent with this hypothesis is the finding that starch accumulates in *Chlamydomonas reinhardtii* flagellar mutants.[9] Paralyzed flagellar mutants were shown to store a significantly greater amount of starch than the motile wild type. The increase in starch was found to be significant relative to protein, chlorophyll, and cell number. Since one of the major energy consuming components of flagellar systems is the dynein-ATPase of the microtubules which power these organelles,[10] it is possible that motor molecules, such as kinesin and dynamin in other systems, also consume considerable quantities of energy.

Genetic makeup likely influences the degree to which an individual tends to store fat. Genetic polymorphism is a term that in the strict sense denotes that at least 2% of the general population is heterozygous at a given locus, that is, there are variations with a normal range, or at least genetic patterns that are not responsible for specific syndromes. Genetic polymorphism might be a reason for the relatively minor dissimilarities in the segments of the spectrum including lean and moderately obese persons. Polymorphism might involve one or more cytoskeletal proteins mediating or regulating biomechanical function(s), or a protein requiring appreciable quantities of energy for its motions. Variability would then be expressed by relatively small disparities between individuals in energy entrapment for biomechanical-mobile processes, eventually resulting in different body fat contents under similar environmental conditions.

Environmental factors also influence the amount of fat an individual stores. The lipid composition of the diet, particularly sustained ingestion of specific fatty acids, is reflected by the lipid composition of cellular membranes. For example, a diet enriched in such polyunsaturated fatty acids as linoleate results in a greater membrane content of this lipid, with an associated increase in "membrane fluidity".[11,12,13] This modification is featured by higher lateral mobility of such membrane components as lipids and (glyco)-proteins. Methods have become available for the quantification of both lateral and rotational mobility of membrane constituents.[11,14] According to the hypothesis, modification of "membrane fluidity" would alter the extent of "biomechanical-mobile" activity. Increased "fluidity" would accelerate (glyco)-protein mobility, exacting a greater input of energy. Less energy would then remain for chemical storage.

In any case, the hypothesis suggests that drugs that interfere with the mechanical functions of the cytoskeleton and associated structures, or with molecular mobility, would decrease energy utilization, an effect that if sustained would have an impact on energy distribution.

It has been clinically observed that patients taking such psychotropic agents as phenothiazines become obese.[1,15] While this association has been ascribed to overeating and decreased physical activity, it might also be due to dampened "biomechanical-mobile" activity. Phenothiazines are known to inhibit processes mediated by calmodulin-Ca$^{2+}$, a complex required for a number of cytoskeletal functions.[16] It has also been observed that agents that interfere with cytoskeletal functions, cytochalasin B, colcemid, and trifluoperazine, can lead to accumulation of triacylglycerol in cultured human preadipocytes.[17,18]

Conversely, agents that stimulate "biomechanical-mobile" activity would, by leading to a greater dissipation of energy, result in a contraction of body fat content. It has been shown, for example, that administration of a combination of ephedrine and caffeine over eight weeks to dieting females resulted in a greater loss of body fat compared to a control group on an otherwise similar diet.[19] This result was obtained even though overall weight loss in both groups was about the same.

Examples of other compounds for treatment against obesity have appeared recently in the patent literature. U.S. Pat. No. 5,300,298 (LaNoue, Apr. 5, 1994) describes the use of certain 8-phenylxanthines substituted in the 3- or 4-position of the phenyl group by an alkenylene, alkenyleneoxy, alkynylene or alkynyleneoxy bearing a terminal acetic grouping in a method of treating obesity. WIPO patent application published under No. 9402150 (Feb. 3, 1994, Smithkline Beecham PLC) describes the use of 1,3-dicyclopropyl-8-amino-xanthine for the treatment of obesity.

There is other supporting evidence for the hypothesis, which evidence is currently known only to the inventors. In experiments, which are described in greater detail below, kinesin heavy chain mutants (khc$^{1rs}$) of the *Drosophila melanogaster* exhibited greater growth and significantly greater triacylglycerol accumulation (P<0.01) than the khc$^6$ strain used as a control. It has also been found that kinesin mRNA levels in subcultured preadipocytes are higher in lean persons than in obese persons.

Finally, before proceeding to describe the invention, it should also be said that any anti-obesity agent, to be useful, must be safe to administer. It must be obtainable in a therapeutically pure form at a reasonable cost. Minimal side effects are of course important. Ease of administration is important too. A particularly useful agent would be available in pill form and be absorbed through the lining of the alimentary canal of a human being, although other routes of administration might be suitable. The agent should be highly effective. A pill that could be taken periodically, say daily, would be suitable.

The invention provides a method for the screening of an agent to determine whether or not it would be useful as an anti-obesity agent. The method includes determining whether such agent stimulates micromotion of cells in vitro. An agent which stimulates cellular micromotion is considered useful as an anti-obesity agent and is a candidate for further testing to determine its particular effectiveness, relative to known anti-obesity agents, for example.

According to a preferred method of the invention, micromotion activity of cultured human preadipocytes is measured. Preadipocytes are not the only cellular candidates that could be used but they are considered preferable. Agents which cause differentiation of the cells into adipocytes could also be identified when the method of the invention is applied to preadipocytes. It is thought that an agent that causes such differentiation in vitro would be a less likely candidate for an anti-obesity agent, as the creation of a greater number of adipocytes would be undesirable.

A number of methods for measuring micromotion are known. One such method is video-enhanced microscopy, a protocol involving such microscopy being detailed further below in connection with experiments involving caffeine.

Micromotion measurements were also carried out by the inventors using an electric cell-substrate impedance sensor by which cell motions on the scale of nanometers are manifested as fluctuations in the impedance of small gold film electrodes that serve as cell substrata.[20]

Once a compound has been found to be a potential anti-obesity agent according to the invention described herein, the safety, selectivity, and efficacy of the putative pharmacologic agent can be established by standard testing of experimental animals, and by clinical trials.

One such compound, 1-carboxyethyl-3,7-dimethylxanthine, has been identified:

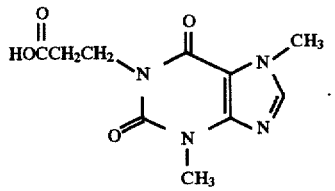

Before describing the invention as it involves micromotion measurements, procedures and results involving *Droso-*

*phila melanogaster* kinesin heavy chain mutants and kinesin mRNA measurements will be described.

BRIEF DESCRIPTION OF DRAWINGS

Reference is made in this specification to attached drawings, in which:

FIGS. 4(a), (b) & (c) show schematically analysis of intracellular motion using enhanced video images of cellular components. Pixels of objects that move, i.e., the black dot in FIGS. 4(a) (time 1) and 4(b) (time 2), which represents a vesicle moving along a microtubule, are the only pixels which have positive values in the final substracted image of FIG. 4(c) (|time 1–time 2|). The larger the positive value in summation of all the pixels in the subtracted image, the greater is the motion between the original two images.

FIG. 6 shows measurement of nanometer cellular motions by an electric cell-substrate impedance sensor by means of a representative photomicrograph of confluent human preadipocytes grown on a gold electrode. Bar=100 μm.

Figure 1A:
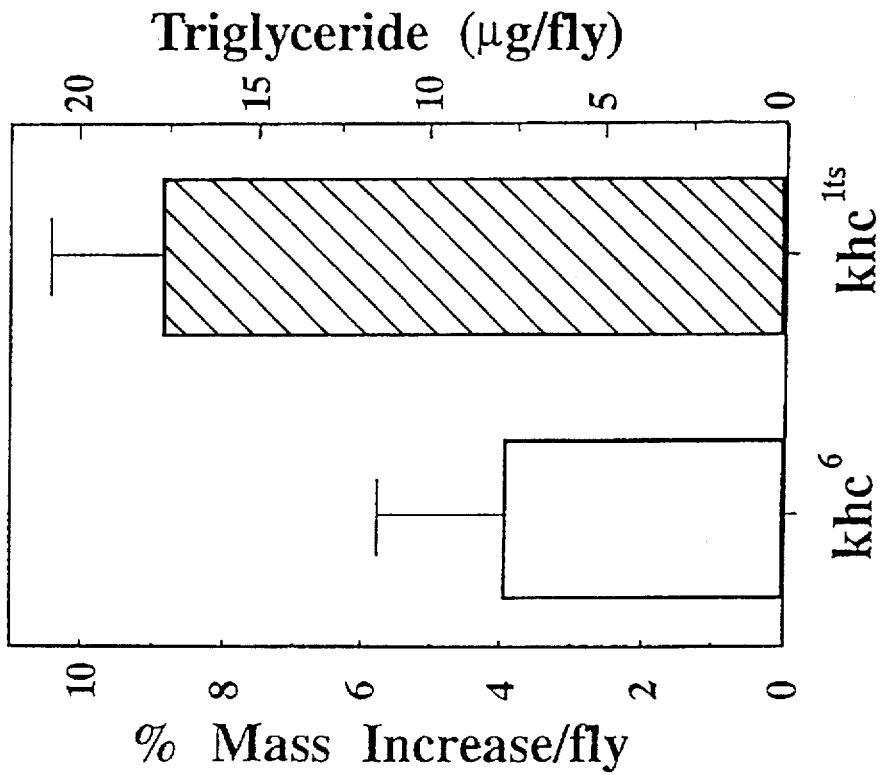
FIG. 1 shows a comparison of control (khc$^6$) and mutant (khc$^{1rs}$) *Drosophila melanogaster* males. A) percent mass increase per fly over the period of incubation. Means ±S.E.M. are shown (P=0.07; N=6). B) Level of triacylglycerol per fly (μg/fly). Means ±S.E.M. are shown (P<0.01; N=6).

METHODS: *Drosophila Melanogaster* and mRNA Measurements of Human Preadipocytes

Drosophila Experiments. Kinesin heavy chain mutants (khc$^{1s}$ and yw;pr khc$^6$/CyO[y$^+$]) of *Drosophila melanogaster* kindly provided by Dr. W. M. Saxton) were maintained on standard soft medium (0.75% agar, 7% molasses, 6% cornmeal, and 0.8% killed yeast) seeded with live yeast in 500 ml bottles at 20° C.[21] Analysis of growth and triglyceride contents was preformed on groups of 10 males incubated for 5 days in 8 dram vials containing standard soft medium without live yeast. Carbon dioxide anaesthetized flies were weighed before and after the incubation period. Triglycerides from Bligh-Dyer[22] extracts of sonicated flies were analyzed by high temperature GLC following isolation of the total neutral lipid fraction by thin layer chromatography (courtesy of Dr. A. Kuksis). Tridecanoin was used as internal standard.

Culture of Preadipocytes. Preadipocytes were isolated and grown from human adipose tissue as previously reported.[23] Human omental adipose tissue was obtained, following informed consent, from persons undergoing elective abdominal surgery. The body mass index (BMI, kgm$^{-2}$) was used as an indicator of degree of obesity. Cells were grown in complete alpha MEM supplemented with 15% fetal bovine serum (Gibco Laboratories, Grand Island, N.Y.), 15 mM Hepes, and antibiotics. A more detailed description is given below in connection with isolation and culture of preadipocytes for use in screening anti-obesity agents through cell-substrate impedance measurements.

Reverse transcription-polymerase chain reaction (RT-PCR). Total RNA was extracted, 1 µg was quantified spectrofluorometrically, and reverse-transcribed as previously reported.[24] Briefly, the RNA (total volume 10 µl) was incubated with 300 pmol of random hexanucleotide primers and 10 U of RNAguard (Pharmacia) at 65° C. for five minutes and then quenched on ice. To the mixture, 10 U RNAguard, reverse transcription (RT) buffer [Gibco; final concentration, 50 mM Tris-HCl (pH 8.3), 75 mM KCl, 3 mM MgCl$_2$, 10 mM dithiothreitol], 1 mM of each DNTP (Boehringer Mannheim), and 200 U of Moloney murine leukemia virus reverse transcriptase (Gibco) were added to a final volume of 20 µl. The mixture was incubated at 37° C. for 120 min, then stopped by incubation at 95° C. for 5 min and diluted to 100 µl with autoclaved distilled water. This new RT mix was then stored at −70° C.

Thermal cycling of 4 µl of each RT mix was performed with human heavy chain kinesin primer sequences provided by Josh Niclas (upstream primer: 5'-GCGCGTTCCCTGCMGACT GAG-3' (SEQ ID NO:1); downstream primer: 5'-GTTTGTCCATATGCAAATATTGTTCC-3') (SEQ ID NO:2) obtained from the Pharmacia Biotechnology Service Centre at the Hospital for Sick Children (Toronto, Ontario, Canada) in the following PCR mixture: 0.2 mM of each DNTP, 50 mM KCl, 10 mM Tris-HCl (pH 9.0 at 25° C.), 0.1% Triton X-100, 2 mM MgCl$_2$, 0.5 U Taq polymerase (Promega Corp., Madison, Wis.), 1 µM upstream and downstream primers (total volume 20 µl). An equal volume of mineral oil (20 µl) was layered on top of the mixture and the amplification was performed in a Perkin-Elmer Cetus thermocycler (model 480, Norwalk, Conn.) using the following parameters for kinesin denaturation 94° C. 1 min., annealing 63° C. 2 min, extension 72° C. 3 min for 35 cycles. The expect product size was 325 bp. The resultant products and a 100 bp DNA ladder (Pharmacia) were visualized with ethidium bromide on 1.5% agarose gels. Bands were quantitated using video analysis.

RESULTS & COMMENTS:

*Drosophila Melanogaster* and mRNA Measurements of Human Preadipocytes

Figure 1B:
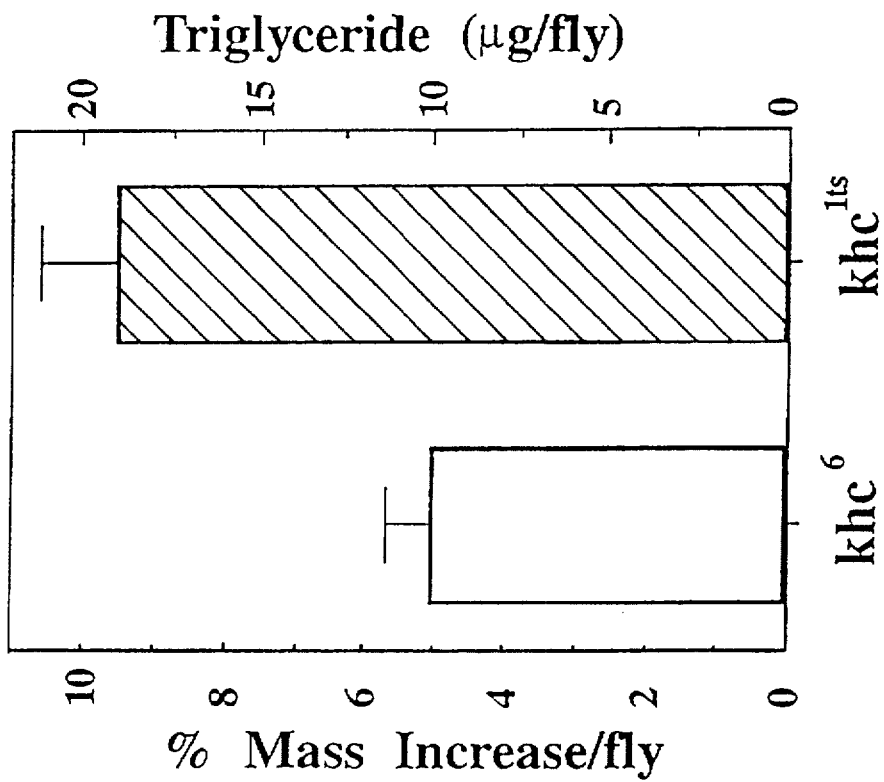

Analysis of the Drosophila kinesin heavy chain mutants indicated greater growth and significantly greater triacylglycerol accumulation (P<0.01) in the khc$^{1s}$ strain than the khc$^6$ (Control) strain as indicated in FIG. 1. However, there was no significant difference in the glyceride composition, as determined by carbon number, between the strains (data not shown). Further, the composition of fatty acids in the triacylglycerols was similar to previously reported data[25] for flies grown on a cornmeal molasses medium. See Table One.

TABLE ONE

| Fatty Acid Composition of Lipids from *Drosophila melanogaster* Mutants | | |
|---|---|---|
| Acids | FFA | TG |
| 14:0 | 9.4 | 11.2 (16.3)* |
| 14:1 | trace | trace |
| 16:0 | 37.7 | 28.8 (20.8) |
| 16:1 | 2.5 | 25.8 (20.8) |
| 18:0 | 25.9 | 5.7 (4.0) |
| 18:1 | 20.6 | 24.2 (25.8) |
| 18:2 | trace | 4.3 (7.1) |
| 18:3 | trace | trace (2.0) |

*Literature values for triglyceride fatty acids of cornmeal-molasses grown *Drosophila melanogaster* mutants.[25]

Figure 2:
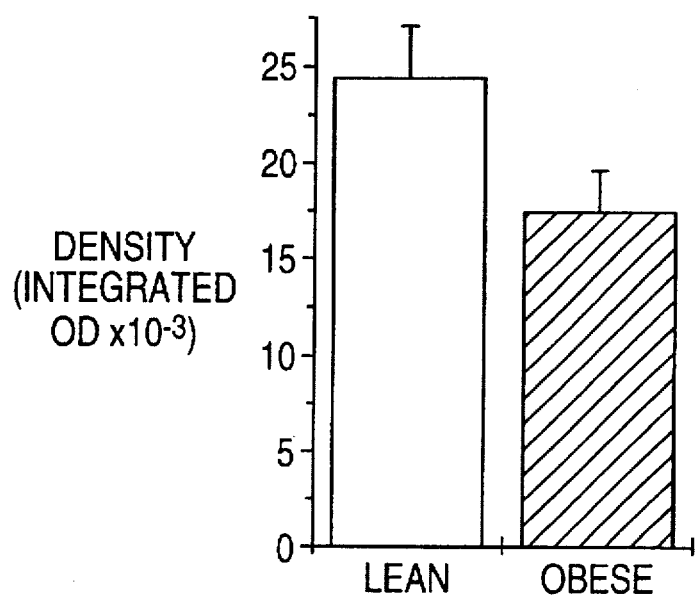
FIG. 2 shows relative levels of kinesin mRNA in human omental preadipocytes. Total RNA isolated from the preadipocytes was reverse-transcribed and amplified using the polymerase chain reaction (35 cycles; 94° C. 1 min, 63° C. 2 min, 72° C. 3 min). The product was electrophoresed in a 1.5% agarose gel and stained with ethidium bromide. Predicted size of the PCR product for glycerophosphate dehydrogenase was 325 bp. M: 100 bp ladder; Lean: preadipocytes from lean individuals (BMI 22.2±1.2; Mean±SEM) Obese: preadipocytes from obese individuals (BMI 42.6±2.3; Mean±SEM).
Figure 3:
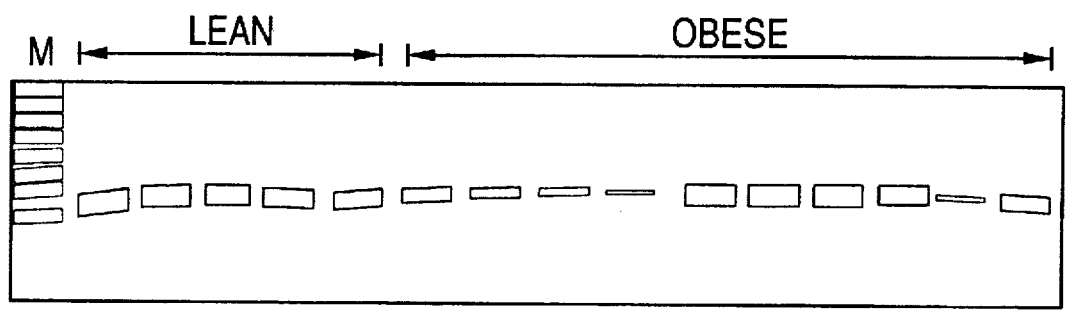
FIG. 3 shows densities (Mean±S.E.M.; P=0.062) of the kinesin PCR products.

Expression of kinesin mRNA in subcultured preadipocytes from 5 lean individuals (BMI 22.2±1.2; Mean±SEM) and 10 obese individuals (BMI 42.6±2.3; Mean±SEM) was analyzed by RT-PCR. See FIG. 2. While there was considerable variation in kinesin mRNA levels, cells from lean persons tended (P=0.062) to express greater mRNA levels than those obtained from obese persons. See FIG. 3.

It is believed that because subcultured cells are many generations removed from the in vivo state that differences between preadipocytes from massively obese and lean subjects should reflect intrinsic cellular properties probably indicative of unique genetic factors. Working in subculture should preclude any differences in the differentiation state of preadipocytes from different people as human preadipocytes lose their ability to differentiate after the first subculture.[26] Use of cells at an equivalent stage of differentiation (a process in which motile fibroblast-like cells become relatively immotile storage cells) is a consideration as suppression of genes encoding cytoskeletal elements, e.g. b-actin and a-tubulin, has been shown to occur during this process.[27,28] A possible consequence of a decrement in kinesin expression would be a reduced number of motors able to consume ATP in cells from the obese with the resulting energy surplus being available for storage.

METHODS: Anti-obesity Agent Screening through Computer-enhanced Video Microscopy Treatment of Preadipocytes. To quantify general motion, preadipocyte cells were grown as monolayers in Alpha Minimal Essential Medium (Alpha MEM) containing 15% fetal bovine serum at 370° C. in humidified air containing 5% $CO_2$. Sparse cultures were prepared on 18×18 mm glass coverslips in 35 mm dishes or on glass coverslips in a Bionique cell culture chamber for the measurements. After washing the cultures twice with saline, the cells were incubated at 370° C. for 12 to 16 hours in Alpha MEM containing 0.5% fetal bovine serum, buffered with 15 mM HEPES.

Description of Computer-Enhanced Video Microscopy. Using cultured preadipocytes, this technique enables detection of as little as a 5% augmentation in cytoskeletal motility. Video-enhanced microscopy offers a view of optically sectioned whole living cells at magnifications up to about 20,000× and with the ability to detect structures as small as microtubules (25 nm). It is possible to investigate and interpret, at the ultrastructural level, structures and processes that can be seen to function in the living state by video-enhanced microscopy.[29]

Enhancement can be achieved by combinations of optical, photographic, or electronic means. Two main optical approaches are well known: phase-contrast and differential interference contrast (Nomarski) microscopy.[29] Electronic means are the most powerful approach, because the combination of analogue and digital enhancement procedures can reveal new information in optical images that is invisible to the eye and could not be captured on film.

Cultured cells, such as preadipocytes, fibroblasts, epithelial cells, neurones in primary culture, etc., can be observed using computer-enhanced video microscopy. In general, more fine details are seen in cells that are thin, transparent, and lacking in highly refractile (scattering) or birefringent features. The microtubule component of the cytoskeleton can be seen with computer-enhanced videomicroscopy. It is best seen in thin portions of fibroblasts and preadipocytes, where cytoplasmic transport can be clearly seen.[30] Various organelles and other cytoplasmic particles move along these microtubules at average velocities from 1 to 3.5 μm/sec. That particle motion occurs only in contact with microtubules has been confirmed by parallel immunofluorescence. Particles can switch from one microtubule to another or can reverse direction on the same microtubule. It has been confirmed by correlated videomicroscopy and electron microscopy that particles can move in both directions along the same single microtubule.[31]

The stage of the phase-contrast microscope (Nikon Canada Instruments Inc.) was maintained at 37° C. by an air curtain incubator. Microscopic images were detected by a TV camera (Hamamatsu Photonics Co.) and transmitted to the image processing system (Universal Imaging Corp.). Processed video images were recorded in a U matic video cassette taperecorder (Sony Co.) for subsequent off-line analysis.[32]

Phase-contrast microscopic images of living cells recorded in the video tape recorder were input to the central processing unit of the imaging system. The visualization and quantitative analysis of morphological changes were performed by the programmed trace mode of the imaging system. The principle of the image processing for the detection of dynamic morphological changes is summarized as follows. The microscopic analogue image from the TV camera at time 0 is converted to the digital image of a matrix consisting of 540×480 pixels with 16 bit pixel resolution, and input and frozen in buffer A. After the interval time period (say 5 seconds), the image at time 0 (contents of buffer A) is transferred to buffer B, the digital image from the microscope at that time (time 1) is then input in buffer A, and the absolute value of the difference between buffer B and buffer A (corresponding to the difference between the images at time 0 and at time 1), is calculated and stored in buffer C. These processes are repeated for 100 seconds, and the content of buffer C corresponding to the accumulation of frames of trace intensity of microscopic images are obtained. The contrast of the accumulated trace image is then digitally enhanced. The moving portion of the cell interior is thus expressed as a white trace whose intensity is dependent on the magnitude of the movement. An appropriate window is set up to define the processed frame. The total intensity of pixels within the window is digitally counted. A photographic record is taken directly from the video monitor display.[32]

RESULTS & COMMENTS:

20 Anti-Obesity Agent Screening through Computer-Enhanced Video Microscopy

FIGS. 4(a), (b) and (c) show schematically, analysis of intracellular motion using enhanced video images of cellular components. Pixels of objects that move are indicated by the black dots shown in FIGS. 4(a) and 4(b). The dots shown in FIGS. 4(a) and 4(b) are taken at time 1 and time 2 and the difference in the locations of the dots indicates movement of a vesicle along a microtubule between the times |time 1–time 2|at which the two images are obtained. These are the only pixels which have positive values in the final substracted image of FIG. 4(c). The larger the positive value in summation of all the pixels in the subtracted images, the greater is the motion between the original two images.

Figure 5:
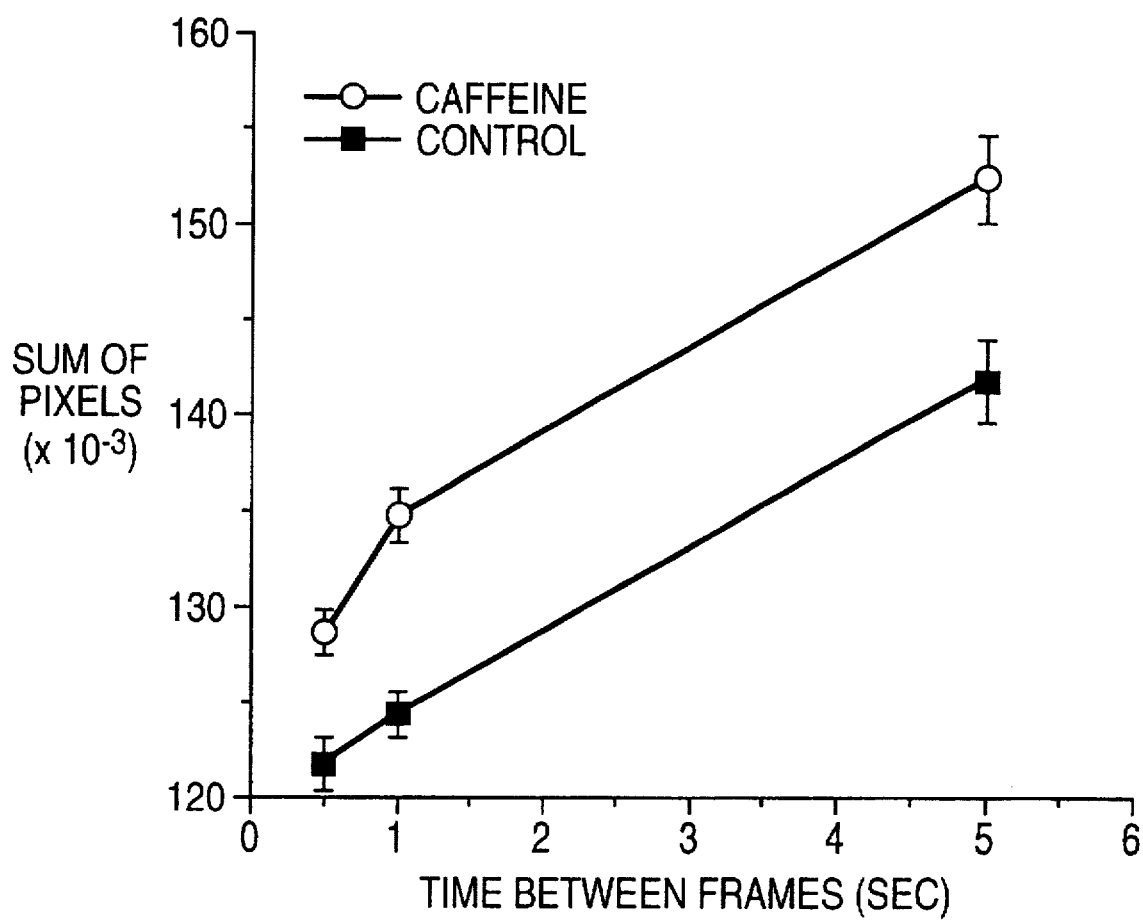
FIG. 5 is a graphical representation of results obtained using the method described in connection with FIGS. 4(a) to 4(c) using human preadipocytes before (○) and after (■) treatment with 10 mM caffeine. The images recorded on videotape were played back through a computer with the time between images, i.e., time 1 and time 2, at 0.5,1 and 5 seconds for at least one minute and averaged. Points shown are the means±standard error.

FIG. 5 is a graphical representation of results obtained using the method described in connection with FIGS. 4(a) to 4(c). Human preadipocytes were treated with caffeine, measures being taken before (○) and after (■) treatment with 10 mM caffeine. The images recorded on videotape were played back through a computer with the time between images, i.e., time 4 and tim 2, at 0.5,1 and 5 seconds for at least one minute and averaged. Points shown are the means± standard error.

METHODS: In vitro Micromotion Analysis of Human Preadipocytes of Lean and Obese Subjects through Impedance Measurements of a Cell Substrate Culture of Preadipocytes. Preadipocytes were prepared as they were for mRNA analysis, described above.

Micromotion Analysis. Cell motions at the manometer level were measured in confluent cultures of human preadipocytes using electric cell-substrate impedance sensor analogous to the one described by Giaever and Keese.[33,34] The cells were grown on large and small gold electrodes evaporated onto Petri dishes and the impedance of an applied current was measured with computer-controlled lock-in amplifiers The in-phase voltage was collected every 3.4 s concurrently for cells from a lean person and cells from an obese person. Numerical analyses were performed analogous to the variance method described by Lo et al.[20] Statistical and numerical analyses were performed with Microsoft Excel 4.0 and Origin 2.67 on the Sunnybrook Health Science Centre Computer Network. A more detailed description is given later in connection with screening of potential anti-obesity agents.

Figure 7A:
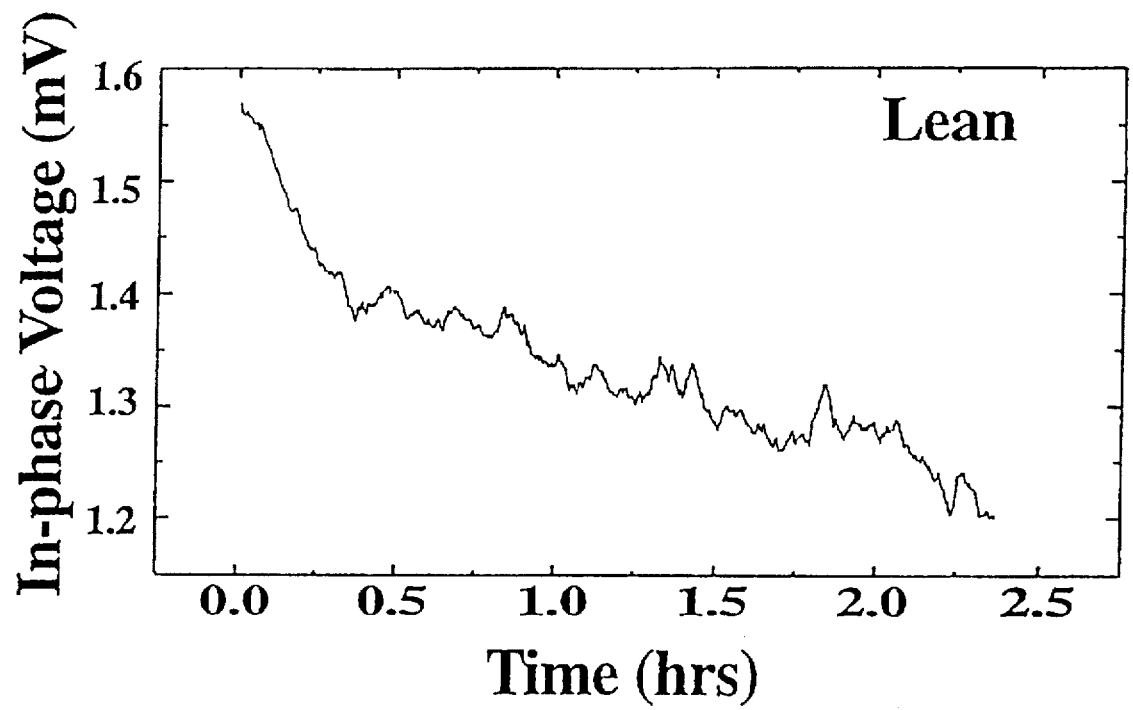
FIG. 7 shows measurement of nanometer cellular motions. Representative in-phase voltage for preadipocytes from lean (upper plot) and obese (lower plot) individuals were measured for 2.5 hours, the fluctuations in the curve for preadipocytes from the lean subjects appearing to be greater than those for preadipocytes from the obese individuals.
Figure 7B:
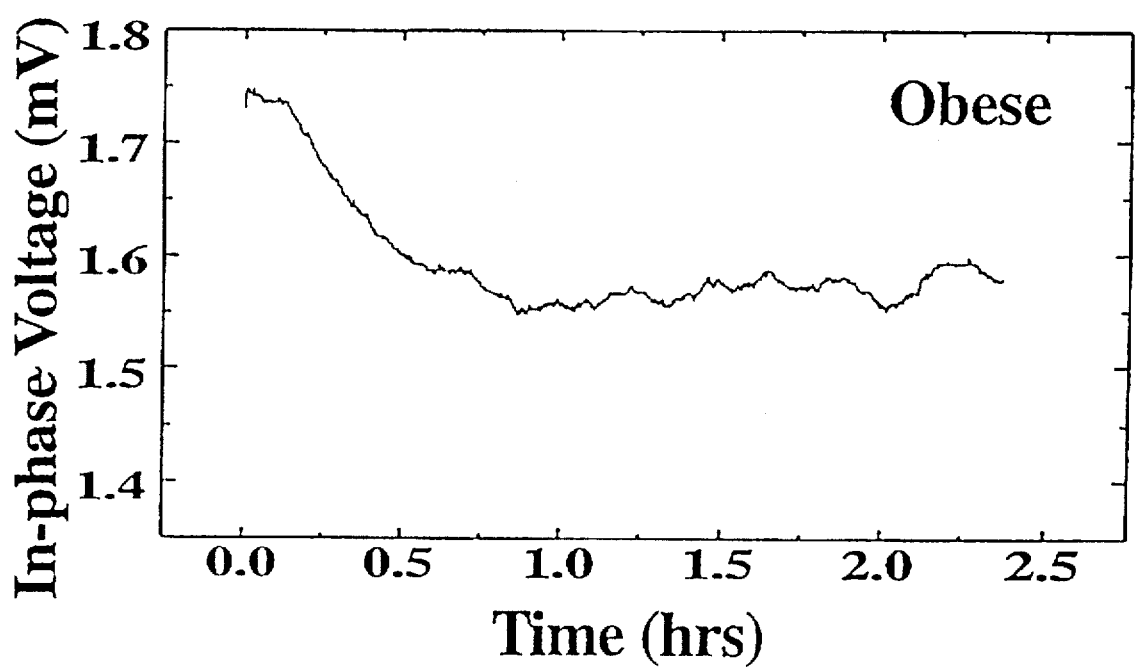
Figure 8A:
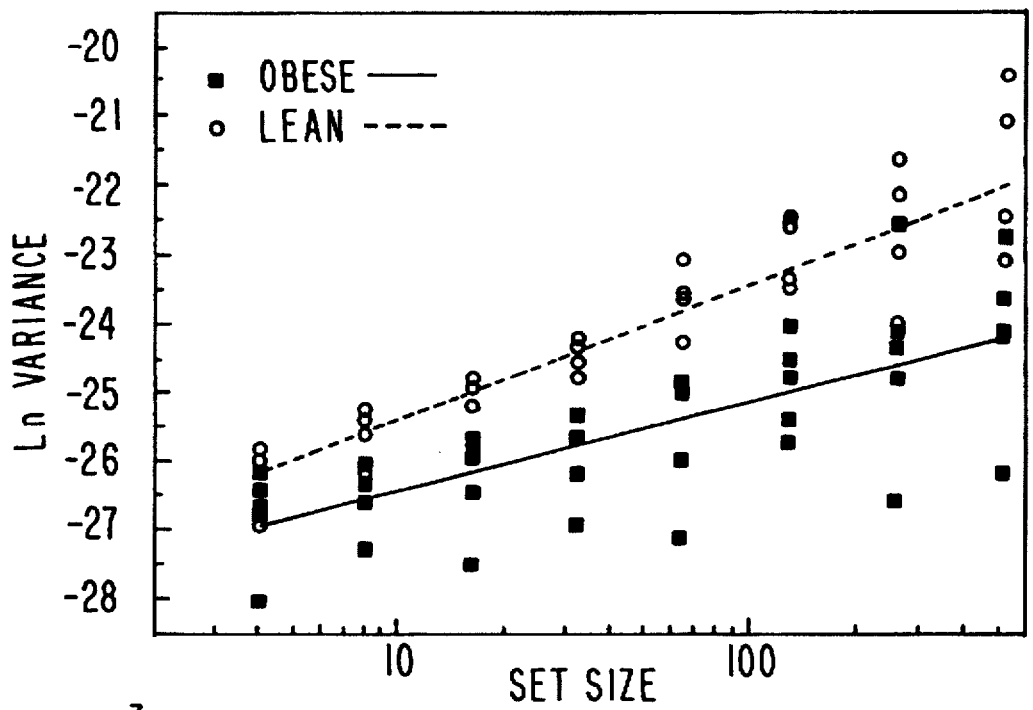
FIG. 8(a) shows the calculated average variance of the data from FIG. 7 for different sampling periods plotted as a function of the same periods, the calculated variance being greater in the lean data, as expected from the initial curves.
Figure 8B:
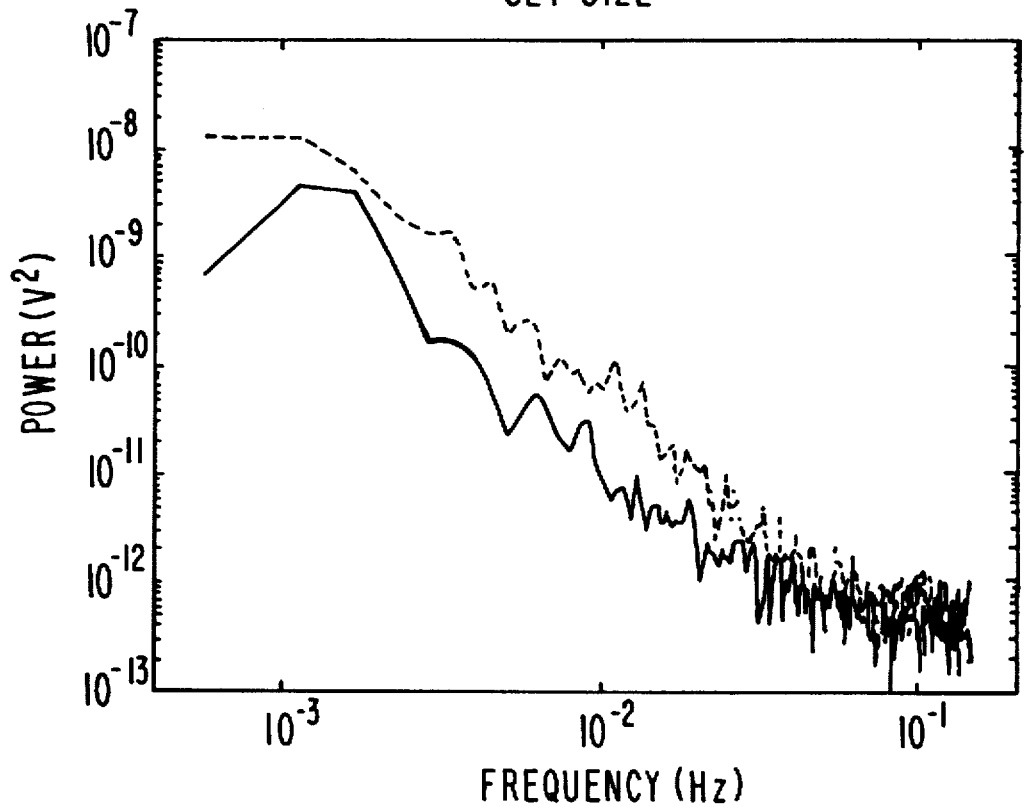
FIG. 8(b) are power spectra of the lean and obese data sets, the data set from the lean having a higher power curve curve indicating a greater frequency of impedance changes.
Figure 9:
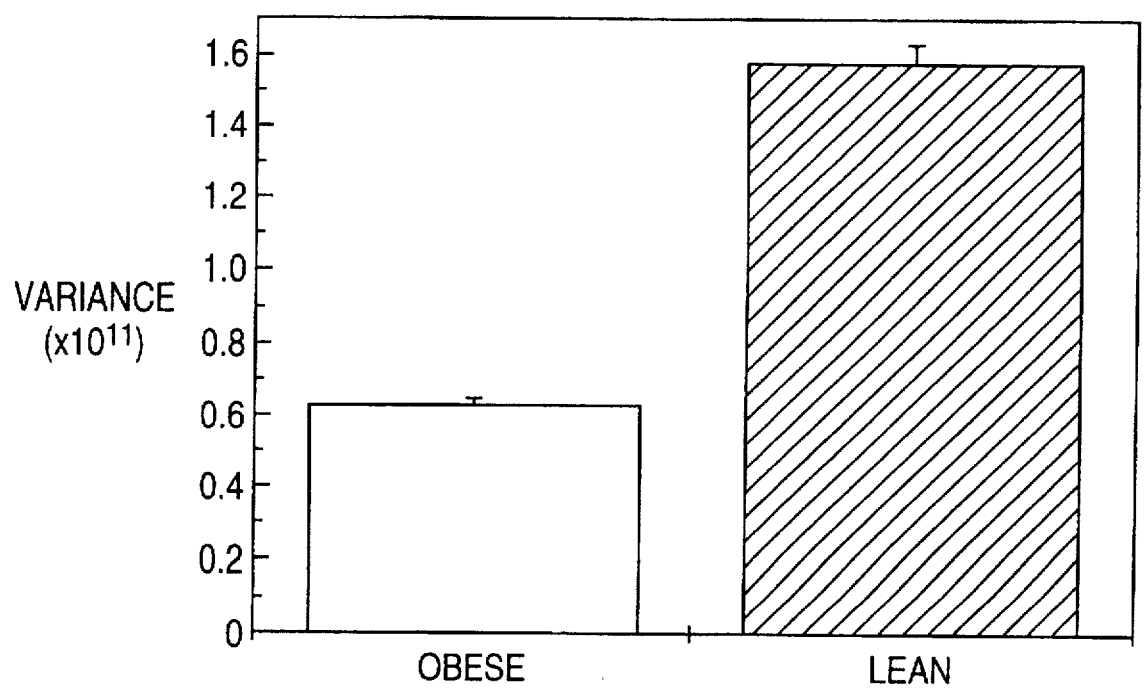
FIG. 9 shows the average variance of voltage fluctuation of cells from lean and obese subjects. Cells from lean individuals had greater variance than those obtained from obese subjects (P<0.03; n=10). Data are represented as mean ±standard error.

RESULTS & COMMENTS:

In vitro Micromotion Analysis of Human Preadipocytes of Lean and Obese Subjects through Impedance Measurements of a Cell Substrate The measured voltage did not fluctuate above noise, essentially "flat-line", in control analyses of an electrodes without cells or cells after fixation with a 10% formalin (data not shown). Cells from 4 lean (BMI 21.5±1.2; Mean±SEM) and 4 (BMI 40.5±6.1; Mean±SEM) obese subjects were grown on gold electrodes and impedance fluctuations recorded. See FIG. 6. Representative recordings obtained are shown in FIG. 7. Numerical analysis of the variance of the data revealed that the fluctuations were greater in cells from the lean individual compared to preadipocytes from the obese person as seen in FIG. 8. Cumulative analysis of all of the subjects' preadipocytes showed that cells from lean individuals had greater ($P<0.05$) "micromotion" activities than those obtained from obese persons. See FIG. 9.

Studies by Lo et al.[20] showed that micromotion detected by electric cell-substrate impedance sensors were dependent on biological activities. Depriving the cells of glucose or incubation at lower temperature (data not shown) reduced the variance of in-phase voltage fluctuations, while treatment with cytochalasin-D partially reduced the voltage changes.[20] It might be relevant that agents that interfere with cytoskeletal functions, i.e. cytochalasin B, colcemid, and trifluoperazine, led to accumulation of triacylglycerol in cultured human preadipocytes.[8] The lower level of fluctuations in preadipocytes from obese persons can be interpreted as an indication reduced energy usage by components of the cytoskeleton.

METHODS: In vitro Anti-Obesity Agent Screening of Preadipocytes by Micromotion Analysis through Impedance Measurements of a Cell Substrate Materials. Alpha minimal essential Eagle's medium ($\alpha$MEM), Hank's balanced salt solution (HBSS), fetal bovine serum (FBS), trypsin, penicillin, and streptomycin can be obtained from Gibco (Grand Island, N.Y.); 250 µm nylon mesh from B & SH Thompson & Co. Ltd. (Scarborough, Ontario, Canada) can be used. Culture flasks and dishes can be obtained from Corning (Corning, N.Y.). Collagenase (Type 11) is obtained from Sigma Chemical Co. (St. Louis, Mo.). 22 µm filters can be from Gelman Sciences Inc. (Montreal, Quebec, Canada).

Isolation and Culture of Preadipocytes. Degree of obesity is commonly determined as percent body weight above reference as determined by the Metropolitan. Life Insurance Company Tables, which were revised and became available in 1983 (Appendix 1). Persons with a body weight<120% of reference or a body mass index (BMI)<27 $kgm^{-2}$ are considered lean. Individuals with a body weight 120–169% of reference or a BMI of 27–37 $kgm^{-2}$ are considered obese. Those subjects with a body weight >170% of reference or a BMI of>37 $kgm^{-2}$ are considered massively obese. Omental fat can be obtained from adult individuals during laparotomy for cholecystectomy, hiatus hernia repair, or gastroplasty, for example.

Human preadipocytes are isolated and cultured as previously described[23], with some minor modifications. All cell cultures are done under sterile conditions using a laminar flow hood, with tissue culture solutions sterilized by passage through 0.22 µm filters. The tissue is minced with scissors to remove the majority of the vascular tissue. Minced tissue is incubated in 30–50 ml of a collagenase solution (1 mg/ml) for 30 minutes at 37° C. with constant stirring. The suspension is filtered through a 250 µm nylon mesh and allowed to stand for 10 minutes to separate the triglyceride-laden floating adipocytes and the stromal-vascular component remaining in suspension. The stromal-vascular fraction is incubated with an erythrocyte lysing buffer (0.154M $NH_4Cl$, 10 mM $KHCO_3$, and 0.1 mM ethylenediaminetetraacetate (EDTA) for 10 minutes at room temperature, to increase cell attachment by removing red blood cells. The stromal-vascular fraction is then centrifuged at 800×g for 10 minutes to yield a pellet consisting mainly of preadipocytes. The pellet is resuspended in complete $\alpha$MEM buffered with 15 mM HEPES (pH 7.2) and supplemented with 15% (vol/vol) FBS, penicillin (200 µg/ml) and streptomycin (100 µg/ml), then plated into 25-$cm^2$ flasks and grown at 37° C. in 5% $CO_2$. The cells are washed 2 to 3 times with HBSS after 14 hours incubation to remove cellular debris. If there is endothelial or mesothelial cell contamination, the cells are subjected to treatment with 0.5 mg/ml trypsin-0.2 mg/ml $Na_2EDTA$ for approximately 1 minute under close scrutiny to differentially detach the contaminating cells, leaving the preadipocytes attached. The culture medium is changed every 3 days, and upon reaching confluence, the cells are detached with trypsin-$Na_2EDTA$ and replated at the desired density in culture flasks/dishes or "micromotion electrodes". Cell counts are performed with a Coulter Counter or manually with a haemocytometer.

Stocks of preadipocyte strains are maintained by trypsin detachment and resuspension in a solution of 10% dimethyl sulfoxide (DMSO) (Sigma Chemical Co.), 90% FBS for storage in liquid nitrogen. Thawing of cells is performed rapidly at 37° C. followed by immediate dilution, by a factor of ten, of the dimethyl sulfoxide solution with $\alpha$MEM containing 15% FBS. After centrifugation at 800×g, the pellet of cells is re-suspended in $\alpha$AMEM with 15% FBS and plated into culture flasks.

Cytotoxicity Assay. Omental preadipocytes are seeded into 96 well plates (5000 cells/well) for testing of the compounds. Various concentrations of the potential drugs are added to the plates. Over various time points the cells are fixed and stained with crystal violet. The amount of crystal violet released into a solution of 5% ethanol/1% sodium laurel sulphate is determined by measuring the absorbance at 570 nm in a micro-plate reader. The absorbance correlates with cell number. The highest concentration of drug not causing a reduction in cell number after 72 hours is used in micromotion tests.

Micromotion Analysis, Materials. Parafilm (American National Can, Greenwich, Conn.), standard 100×15 mm petri dishes (Fisher Scientific Co., Unionville, Ontario, Canada), indium, indium flux, varnish-insulated copper wire (30 AWG; Belden Geneva, Ill.) 1/32" and 0.005" brass for mask, 100 k$\Omega$ resistors, coaxial cables, and RS-232 communication cable.

Equipment. Lock-in amplifiers (Models SR530 and SR510, Stanford Research Systems Inc., Palo Alto, Calif.); sweep/ function generator (Model 180, Wavetek, San Diego, Calif.); personal computers (Model #HP85A, Hewlett-Packard Co., Corvallis, Oreg.) and Macintosh IIx (Apple Computer Inc., Cupertino, Calif.); automatic dicing saw (Model DAD-2H/ 6TM; Disco Corp., Salem, N.H.), vacuum evaporator (Model SE-600-RAP; CHA Industries, Freemont, Calif.), UV-C germicidal light (General Electric Co., Cleveland, Ohio).

Figure 10:
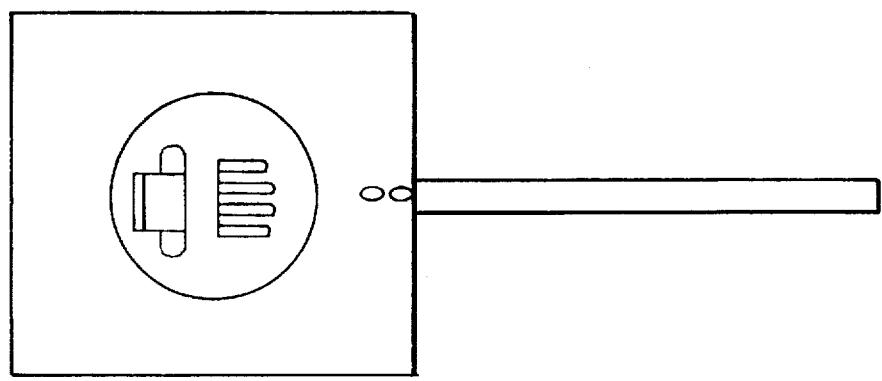
FIG. 10 is a photograph showing the extended portion of a mask for small electrodes.
Figure 11:
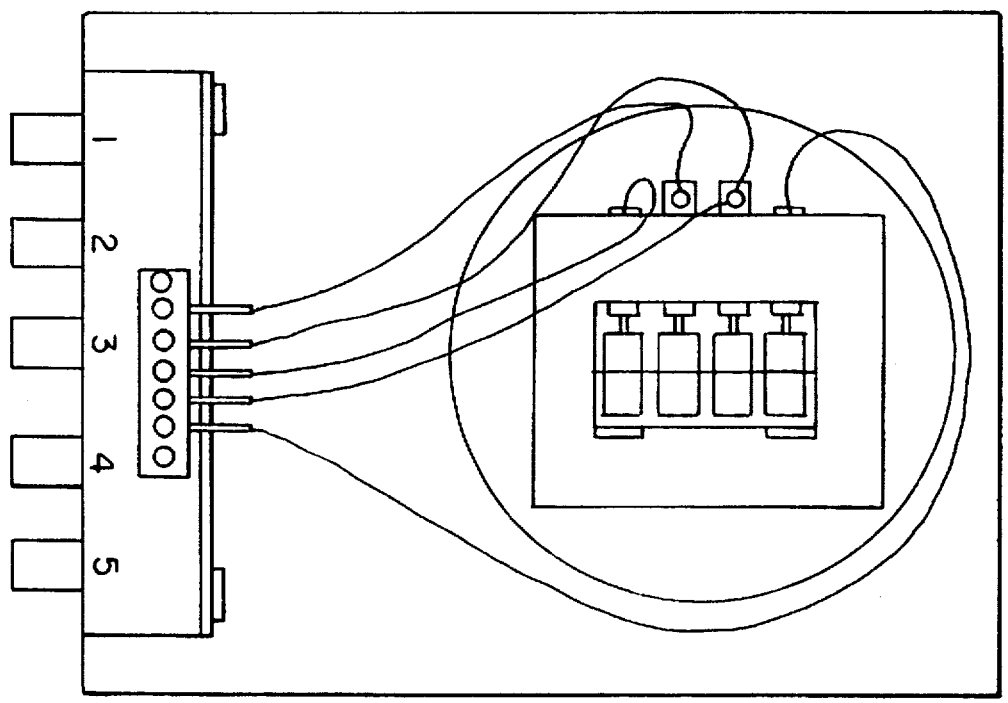
FIG. 11 is a photograph showing the four small assembled electrodes used for micromotion measurements, statistical analysis of the data being shown in Table Two.

Electrode Dish. The mask for the electrodes is constructed from 1/32" brass made to outline one large and four small electrodes. The extended portion of the mask for the small electrodes is composed of 0.005" brass in which slits (200 µm wide) are cut with an automatic dicing saw. See FIG. 10. Gold is evaporated to a thickness of 100 nm onto the bottom of 10 cm petri dishes through the mask in a vacuum evaporator at pressures of $10^{-6}$ to $10^{-7}$ Torr to form the base of the electrodes. Connections to the circuits are made through varnish-insulated copper wires soldered with pure indium directly to the gold. After delineating the areas of one large and four small electrodes with heated parafilm, the plates are treated with strong ultraviolet light, 4 cm from a UV-C germicidal bulb for 10 min, to make the surface of the polystyrene hydrophillic for cell attachment. See FIG. 11.

Measurement of Cellular Motion. Inoculation of electrode containing dishes is at about $1 \times 10^5$ preadipocytes per square centimeter. All measurements are made at least 18 hours following inoculation with cell layers that are judged to be confluent by microscopic observation. The impedance of an applied current (100 mV at 4000 Hz through a 100 kΩ resistor) is measured with the computer-controlled lock-in amplifiers. The in-phase voltage is collected every 3.4 s concurrently for cells from a lean person and cells from an obese person using the program outlined in Appendix II. A baseline is established over a suitable length of time, for example, about 2 hours, and then test compounds previously tested for their cytotoxicity are added and measurement continued for another few, say about four to six hours. Numerical analyses are performed analogous to the variance method, described previously,[20] using a Microsoft Excel 4.0 macro (Appendix III). An increased measured variance as resulting from addition of a compound indicates that the compound is a potential anti-obesity agent.

RESULTS & COMMENTS

In vitro Anti-Obesity Agent Screening of Preadipocytes by Micromotion Analysis through Impedance Measurements of a Cell Substrate The above-described method was applied to 1-carboxyethyl-3,7-dimethylxanthine, compound I:

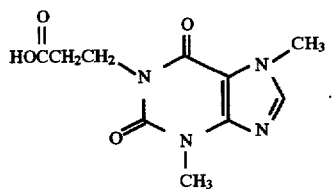

Figure 12:
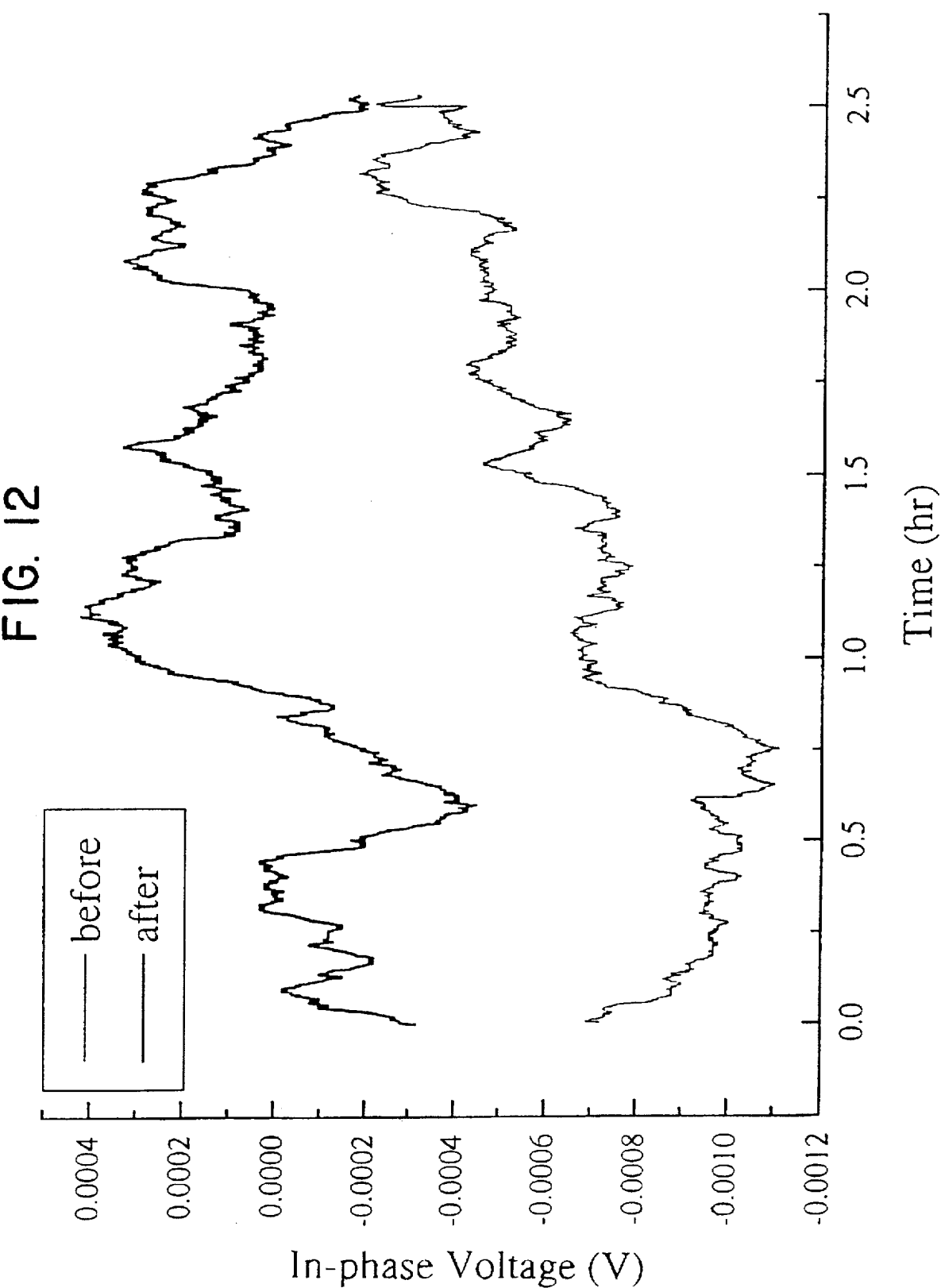
FIG. 12 shows measurement of nanometer cellular motions of representative in-phase voltage for preadipocytes from obese individuals in screening with 2 mM compound I. The lower curve is for untreated cells while the upper curve was taken immediately afterwards of the cells treated with compound I, measurements being taken over 2.5 hours each time.
Figure 13:
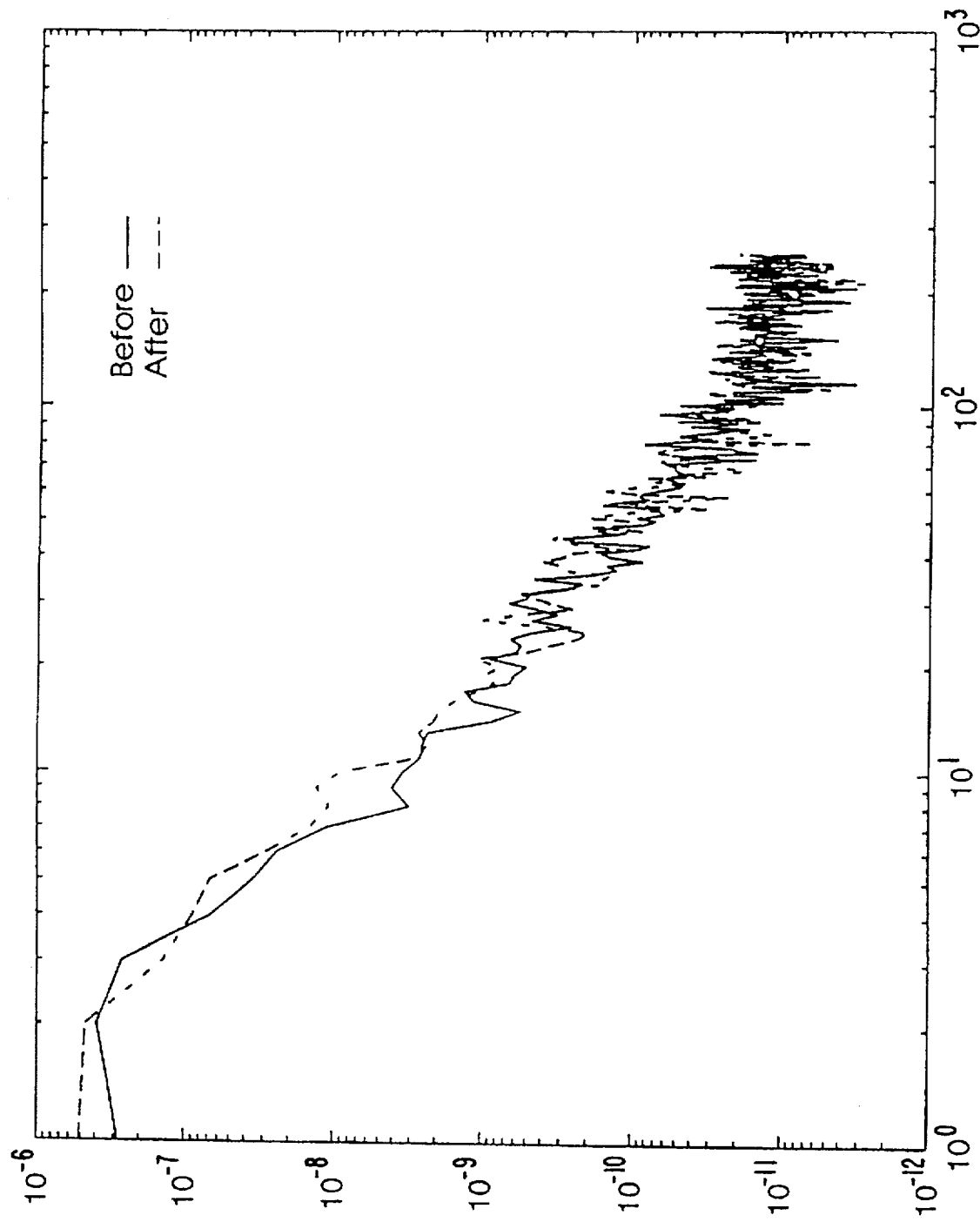
FIG. 13 is a power spectral analysis of the data shown in FIG. 12.
Figure 14:
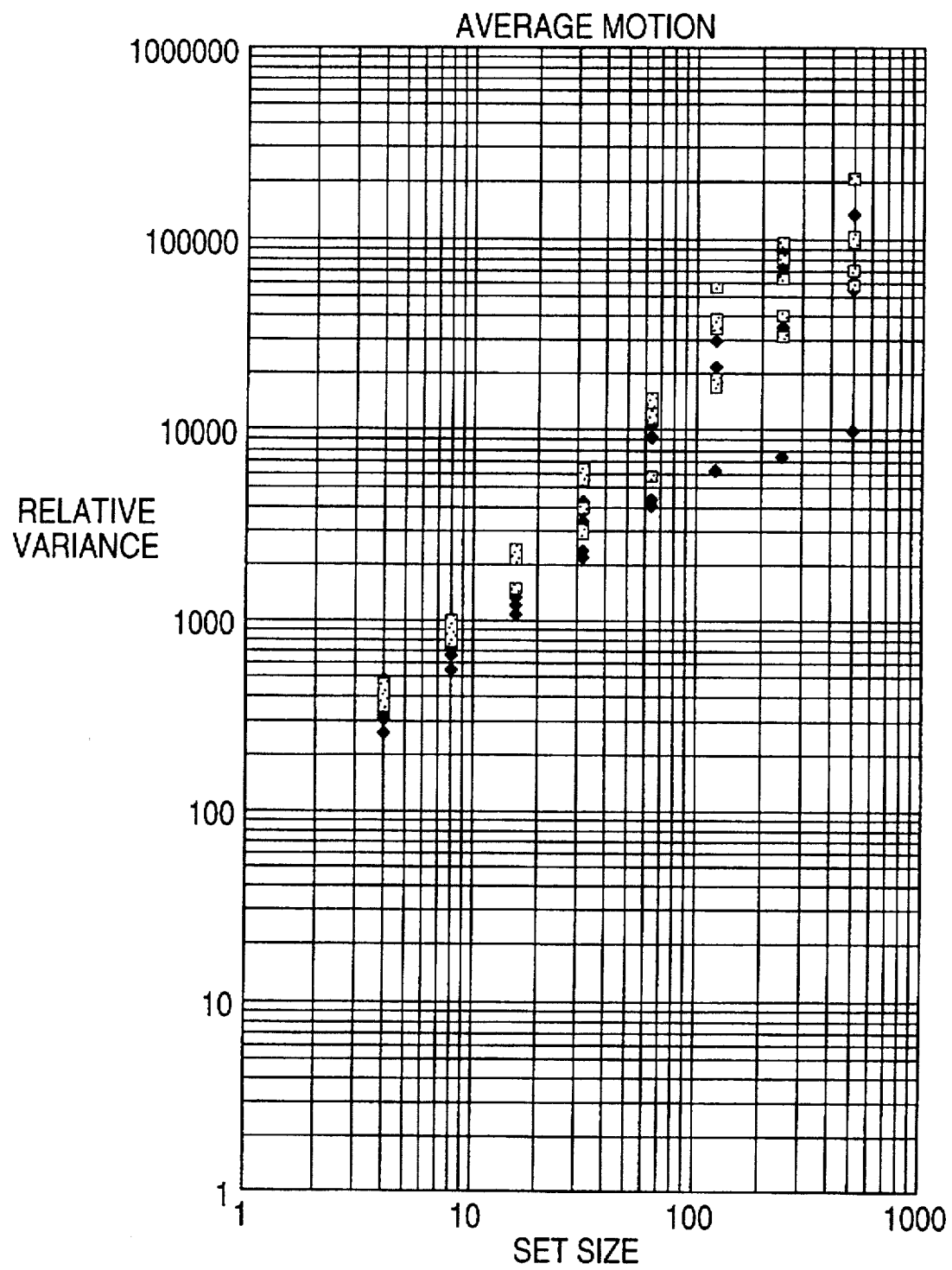
FIG. 14 is a variance analysis of the data shown in FIG. 12 before (♦) and after (■) treatment with 2 mM compound I.

The concentration of compound I used was 2 mM, as determined by the cytoxicity assay described above. Results are shown in FIGS. 12 to 14 and statistical analysis is presented in Table Two. As can be seen, micromotion of the treated cells was enhanced in comparison to the untreated cells.

TABLE TWO t-Test—Paired Two Sample for Means of data shown in FIG. 12

|  | Untreated Cells | Treated Cells |
|---|---|---|
| Mean | −21.4423 | −21.0081 |
| Variance | 4.013819 | 3.722491 |
| Observations | 40 | 40 |
| Pearson Correlation | 0.899773 |  |
| Hypothesized Mean Difference | 0 |  |
| df | 39 |  |
| t Stat | −3.10818 |  |
| P (T ≦ t) one-tail | 0.001753 |  |
| t Critical one-tail | 1.684875 |  |
| P (T ≦ t) two-tail | 0.003506 |  |
| t Critical two-tail | 2.022689 |  |

APPENDIX I

THE 1983 METROPOLITAN HEIGHT AND WEIGHT TABLES, CONVERTED TO METRIC SYSTEM
Weight in Kilograms

| Height Centimeters | Small Frame | Medium Frame | Large Frame |
|---|---|---|---|
| MEN | | | |
| 158 | 58.3–61.0 | 59.6–64.2 | 62.8–68.3 |
| 159 | 58.6–61.3 | 59.9–64.5 | 63.1–68.8 |
| 160 | 59.0–61.7 | 60.3–64.9 | 63.5–69.4 |
| 161 | 59.3–62.0 | 60.6–65.2 | 63.8–69.9 |
| 162 | 59.7–62.4 | 61.0–65.6 | 64.2–70.5 |
| 163 | 60.0–62.7 | 61.3–66.0 | 64.5–71.1 |
| 164 | 60.4–63.1 | 61.7–66.5 | 64.9–71.8 |
| 165 | 60.8–63.5 | 62.1–67.0 | 65.3–72.5 |
| 166 | 61.1–63.8 | 62.4–67.6 | 65.6–73.2 |
| 167 | 61.5–64.2 | 62.8–68.2 | 66.0–74.0 |
| 168 | 61.8–64.6 | 63.2–68.7 | 66.4–74.7 |
| 169 | 62.2–65.2 | 63.8–69.3 | 67.0–75.4 |
| 170 | 62.5–65.7 | 64.3–69.8 | 67.5–76.1 |
| 171 | 62.9–66.2 | 64.8–70.3 | 68.0–76.8 |
| 172 | 63.2–66.7 | 65.4–70.8 | 68.5–77.5 |
| 173 | 63.6–67.3 | 65.9–71.4 | 69.1–78.2 |
| 174 | 63.9–67.8 | 66.4–71.9 | 69.6–78.9 |
| 175 | 64.3–68.3 | 66.9–72.4 | 70.1–79.6 |
| 176 | 64.7–68.9 | 67.5–73.0 | 70.7–80.3 |
| 177 | 65.0–69.5 | 68.1–73.5 | 71.3–81.0 |
| 178 | 65.4–70.0 | 68.6–74.0 | 71.8–81.8 |
| 179 | 65.7–70.5 | 69.2–74.6 | 72.3–82.5 |
| 180 | 66.1–71.0 | 69.7–75.1 | 72.8–83.3 |
| 181 | 66.6–71.6 | 70.2–75.8 | 73.4–84.0 |
| 182 | 67.1–72.1 | 70.7–76.5 | 73.9–84.7 |
| 183 | 67.7–72.7 | 71.3–77.2 | 74.5–85.4 |
| 184 | 68.2–73.4 | 71.8–77.9 | 75.2–86.1 |
| 185 | 68.7–74.1 | 72.4–78.6 | 75.9–86.8 |
| 186 | 69.2–74.8 | 73.0–79.3 | 76.6–87.6 |
| 187 | 69.8–75.5 | 73.7–80.0 | 77.3–88.5 |
| 188 | 70.3–76.2 | 74.4–80.7 | 78.0–89.4 |
| 189 | 70.9–76.9 | 74.9–81.5 | 78.7–90.3 |
| 190 | 71.4–77.6 | 75.4–82.2 | 79.4–91.2 |
| 191 | 72.1–78.4 | 76.1–83.0 | 80.3–92.1 |
| 192 | 72.8–79.1 | 76.8–83.9 | 81.2–93.0 |
| 193 | 73.5–79.8 | 77.6–84.8 | 82.1–93.9 |
| WOMEN | | | |
| 148 | 46.4–50.6 | 49.6–55.1 | 53.7–59.8 |
| 149 | 46.6–51.0 | 50.0–55.5 | 54.1–60.3 |
| 150 | 46.7–51.3 | 50.3–55.9 | 54.4–60.9 |
| 151 | 46.9–51.7 | 50.7–56.4 | 54.8–61.4 |
| 152 | 47.1–52.1 | 51.1–57.0 | 55.2–61.9 |
| 153 | 47.4–52.5 | 51.5–57.5 | 55.6–62.4 |
| 154 | 47.8–53.0 | 51.9–58.0 | 56.2–63.0 |
| 155 | 48.1–53.6 | 52.2–58.6 | 56.8–63.6 |
| 156 | 48.5–54.1 | 52.7–59.1 | 57.3–64.1 |
| 157 | 48.8–54.6 | 53.2–59.6 | 57.8–64.6 |
| 158 | 49.3–55.2 | 53.8–60.2 | 58.4–65.3 |
| 159 | 49.8–55.7 | 54.3–60.7 | 58.9–66.0 |
| 160 | 50.3–56.2 | 54.9–61.2 | 59.4–66.7 |
| 161 | 50.8–56.7 | 55.4–61.7 | 59.9–67.4 |
| 162 | 51.4–57.3 | 55.9–62.3 | 60.5–68.1 |
| 163 | 51.9–57.8 | 56.4–62.8 | 61.0–68.8 |
| 164 | 52.5–58.4 | 57.0–63.4 | 61.5–69.5 |
| 165 | 53.0–58.9 | 57.5–63.9 | 62.0–70.2 |
| 166 | 53.6–59.5 | 58.1–64.5 | 62.6–70.9 |
| 167 | 54.1–60.0 | 58.7–65.0 | 63.2–71.7 |
| 168 | 54.6–60.5 | 59.2–65.5 | 63.7–72.4 |
| 169 | 55.2–61.1 | 59.7–66.1 | 64.3–73.1 |
| 170 | 55.7–61.6 | 60.2–66.6 | 64.8–73.8 |
| 171 | 56.2–62.1 | 60.7–67.1 | 65.3–74.5 |
| 172 | 56.8–62.6 | 61.3–67.6 | 65.8–75.2 |
| 173 | 57.3–63.2 | 61.8–68.2 | 66.4–75.9 |
| 174 | 57.8–63.7 | 62.3–68.7 | 66.9–76.4 |
| 175 | 58.3–64.2 | 62.8–69.2 | 67.4–76.9 |
| 176 | 58.9–64.8 | 63.4–69.8 | 68.0–77.5 |
| 177 | 59.5–65.4 | 64.0–70.4 | 68.5–78.1 |
| 178 | 60.0–65.9 | 64.5–70.9 | 69.0–78.6 |
| 179 | 60.5–66.4 | 65.1–71.4 | 69.6–79.1 |

APPENDIX I-continued

THE 1983 METROPOLITAN HEIGHT AND WEIGHT TABLES, CONVERTED TO METRIC SYSTEM
Weight in Kilograms

| Height Centimeters | Small Frame | Medium Frame | Large Frame |
|---|---|---|---|
| 180 | 61.0–66.9 | 65.6–71.9 | 70.1–79.6 |
| 181 | 61.6–67.5 | 66.1–72.5 | 70.7–80.2 |
| 182 | 62.1–68.0 | 66.6–73.0 | 71.2–80.7 |
| 183 | 62.6–68.5 | 67.1–73.5 | 71.7–81.2 |

Weights at ages 25–59, wearing shoes with 2.5 cm heels and indoor clothing weighing 2.3 kg for men and 1.4 kg for women.

APPENDIX II

Basic Program for controlling the lock-in amplifiers and outputting the readings to the Macintosh IIx.

| | |
|---|---|
| 10 REMOTE 710, 730 | :Tells computer to look or both lock-in Amplifiers |
| 20 OUTPUT 710; "A1" | :Resets the measured voltage to zero |
| 30 OUTPUT 730; "AX" | :Resets the measured voltage to zero |
| 100 FOR M=0 TO 1024 | :The FOR-NEXT statements indicate # of data points collected before the voltage is reset to zero |
| 110 FOR S=0 TO 30 STEP 10 | |
| 120 OUTPUT 710; "Q" | :Request value from LED on Lock-in amplifier Model 510 |
| 130 ENTER 710; A | :Set value from Lock-in amplifier to be A |
| 140 OUTPUT 730; "Q1" | :Request value from channel 1 on Lock-in amplifier Model 530 |
| 150 ENTER 730; B | :Set value from Lock-in amplifier to be B |

APPENDIX II-continued

Basic Program for controlling the lock-in amplifiers and outputting the readings to the Macintosh IIx.

| | |
|---|---|
| 160 DISP M;S;A;B | :Displays time and voltage for each lock-in amplifier. |
| 161 OUTPUT 10 A,B | :Outputs data to the Macintosh IIx via RS-232 port. |
| 170 WAIT 1000; | :Time delay of 1 sec before taking the next reading. |
| 180 NEXT S | |
| 190 NEXT M | |
| 300 PRINT | |
| 310 PRINT | |
| 320 GOTO 20 | :Starts measurement of next data set. |

APPENDIX III

Variance Computation

| | A(*) | B(**) | C | D | E | F |
|---|---|---|---|---|---|---|
| 1 | | | = VAR(A1:A4) | = VAR(A1:A8) | = VAR(A1:A16) | = VAR(A1:A32) |
| 2 | | | = VAR(A5:A8) | = VAR(A9:A16) | = VAR(A17:A32) | = VAR(A33:A64) |
| 3 | | | = VAR(A9:A12) | = VAR(A17:A24) | = VAR(A33:A48) | = VAR(A65:A96) |
| 4 | | | = VAR(A13:A16) | = VAR(A25:A32) | = VAR(A49:A64) | = VAR(A97:A128) |
| 5 | | | = VAR(A17:A20) | = VAR(A33:A40) | = VAR(A65:A80) | = VAR(A129:A160) |
| 6 | | | = VAR(A21:A24) | = VAR(A41:A48) | = VAR(A81:A96) | = VAR(A161:A192) |
| 7 | | | = VAR(A25:A28) | = VAR(A49:A56) | = VAR(A97:A112) | = VAR(A193:A224) |
| 8 | | | = VAR(A29:A32) | = VAR(A57:A64) | = VAR(A113:A128) | = VAR(A225:A256) |
| 9 | | | = VAR(A33:A36) | = VAR(A65:A72) | = VAR(A129:A144) | = VAR(A257:A288) |
| 10 | | | = VAR(A37:A40) | = VAR(A73:A80) | = VAR(A145:A160) | = VAR(A289:A320) |
| 11 | | | = VAR(A41:A44) | = VAR(A81:A88) | = VAR(A161:A176) | = VAR(A321:A352) |
| 12 | | | = VAR(A45:A48) | = VAR(A89:A96) | = VAR(A177:A192) | = VAR(A353:A384) |
| 13 | | | = VAR(A49:A52) | = VAR(A97:A104) | = VAR(A193:A208) | = VAR(A385:A416) |
| 14 | | | = VAR(A53:A56) | = VAR(A105:A112) | = VAR(A209:A224) | = VAR(A417:A448) |
| 15 | | | = VAR(A57:A60) | = VAR(A113:A120) | = VAR(A225:A240) | = VAR(A449:A480) |
| 16 | | | = VAR(A61:A64) | = VAR(A121:A128) | = VAR(A241:A256) | = VAR(A481:A512) |
| 17 | | | = VAR(A65:A68) | = VAR(A129:A136) | = VAR(A257:A272) | |
| 18 | | | = VAR(A69:A72) | = VAR(A137:A144) | = VAR(A273:A288) | |
| 19 | | | = VAR(A73:A76) | = VAR(A145:A152) | = VAR(A289:A304) | |
| 20 | | | = VAR(A77:A80) | = VAR(A153:A160) | = VAR(A305:A320) | |
| 21 | | | = VAR(A81:A84) | = VAR(A161:A168) | = VAR(A321:A336) | |
| 22 | | | = VAR(A85:A88) | = VAR(A169:A176) | = VAR(A337:A352) | |
| 23 | | | = VAR(A89:A92) | = VAR(A177:A184) | = VAR(A353:A368) | |
| 24 | | | = VAR(A93:A96) | = VAR(A185:A192) | = VAR(A369:A384) | |
| 25 | | | = VAR(A97:A100) | = VAR(A193:A200) | = VAR(A385:A400) | |
| 26 | | | = VAR(A101:A104) | = VAR(A201:A208) | = VAR(A401:A416) | |
| 27 | | | = VAR(A105:A108) | = VAR(A209:A216) | = VAR(A417:A432) | |
| 28 | | | = VAR(A109:A112) | = VAR(A217:A224) | = VAR(A433:A448) | |
| 29 | | | = VAR(A113:A116) | = VAR(A225:A232) | = VAR(A449:A464) | |
| 30 | | | = VAR(A117:A120) | = VAR(A233:A240) | = VAR(A465:A480) | |
| 31 | | | = VAR(A121:A124) | = VAR(A241:A248) | = VAR(A481:A496) | |
| 32 | | | = VAR(A125:A128) | = VAR(A249:A256) | = VAR(A497:A512) | |
| 33 | | | = VAR(A129:A132) | = VAR(A257:A264) | | |
| 34 | | | = VAR(A133:A136) | = VAR(A265:A272) | | |
| 35 | | | = VAR(A137:A140) | = VAR(A273:A280) | | |

APPENDIX III-continued

Variance Computation

| | | |
|---|---|---|
| 36 | = VAR(A141:A144) | = VAR(A281:A288) |
| 37 | = VAR(A145:A148) | = VAR(A289:A296) |
| 38 | = VAR(A149:A152) | = VAR(A297:A304) |
| 39 | = VAR(A153:A156) | = VAR(A305:A312) |
| 40 | = VAR(A157:A160) | = VAR(A313:A320) |
| 41 | = VAR(A161:A164) | = VAR(A321:A328) |
| 42 | = VAR(A165:A168) | = VAR(A329:A336) |
| 43 | = VAR(A169:A172) | = VAR(A337:A344) |
| 44 | = VAR(A173:A176) | = VAR(A345:A352) |
| 45 | = VAR(A177:A180) | = VAR(A353:A360) |
| 46 | = VAR(A181:A184) | = VAR(A361:A368) |
| 47 | = VAR(A185:A188) | = VAR(A369:A376) |
| 48 | = VAR(A189:A192) | = VAR(A377:A384) |
| 49 | = VAR(A193:A196) | = VAR(A385:A392) |
| 50 | = VAR(A197:A200) | = VAR(A393:A400) |
| 51 | = VAR(A201:A204) | = VAR(A401:A408) |
| 52 | = VAR(A205:A208) | = VAR(A409:A416) |
| 53 | = VAR(A209:A212) | = VAR(A417:A424) |
| 54 | = VAR(A213:A216) | = VAR(A425:A432) |
| 55 | = VAR(A217:A220) | = VAR(A433:A440) |
| 56 | = VAR(A221:A224) | = VAR(A441:A448) |
| 57 | = VAR(A225:A228) | = VAR(A449:A456) |
| 58 | = VAR(A229:A232) | = VAR(A457:A464) |
| 59 | = VAR(A233:A236) | = VAR(A465:A472) |
| 60 | = VAR(A237:A240) | = VAR(A473:A480) |
| 61 | = VAR(A241:A244) | = VAR(A481:A488) |
| 62 | = VAR(A245:A248) | = VAR(A489:A496) |
| 63 | = VAR(A249:A252) | = VAR(A497:A504) |
| 64 | = VAR(A253:A256) | = VAR(A505:A512) |
| 65 | = VAR(A257:A260) | |
| 66 | = VAR(A261:A264) | |
| 67 | = VAR(A265:A268) | |
| 68 | = VAR(A269:A272) | |
| 69 | = VAR(A273:A276) | |
| 70 | = VAR(A277:A280) | |
| 71 | = VAR(A281:A284) | |
| 72 | = VAR(A285:A288) | |
| 73 | = VAR(A289:A292) | |
| 74 | = VAR(A293:A296) | |
| 75 | = VAR(A297:A300) | |
| 76 | = VAR(A301:A304) | |
| 77 | = VAR(A305:A308) | |
| 78 | = VAR(A309:A312) | |
| 79 | = VAR(A313:A316) | |
| 80 | = VAR(A317:A320) | |
| 81 | = VAR(A321:A324) | |
| 82 | = VAR(A315:A328) | |
| 83 | = VAR(A329:A332) | |
| 84 | = VAR(A333:A336) | |
| 85 | = VAR(A337:A340) | |
| 86 | = VAR(A341:A344) | |
| 87 | = VAR(A345:A348) | |
| 88 | = VAR(A349:A352) | |
| 89 | = VAR(A353:A356) | |
| 90 | = VAR(A357:A360) | |
| 91 | = VAR(A361:A364) | |
| 92 | = VAR(A365:A368) | |
| 93 | = VAR(A369:A372) | |
| 94 | = VAR(A373:A376) | |
| 95 | = VAR(A377:A380) | |
| 96 | = VAR(A381:A384) | |
| 97 | = VAR(A385:A388) | |
| 98 | = VAR(A389:A392) | |
| 99 | = VAR(A393:A396) | |
| 100 | = VAR(A397:A400) | |
| 101 | = VAR(A401:A404) | |
| 102 | = VAR(A405:A408) | |
| 103 | = VAR(A409:A412) | |
| 104 | = VAR(A413:A416) | |
| 105 | = VAR(A417:A420) | |
| 106 | = VAR(A421:A424) | |
| 107 | = VAR(A425:A428) | |
| 108 | = VAR(A429:A432) | |
| 109 | = VAR(A433:A436) | |
| 110 | = VAR(A437:A440) | |
| 111 | = VAR(A441:A444) | |
| 112 | = VAR(A445:A448) | |

APPENDIX III-continued

Variance Computation

| | | | | |
|---|---|---|---|---|
| 113 | = VAR(A449:A452) | | | |
| 114 | = VAR(A453:A456) | | | |
| 115 | = VAR(A457:A460) | | | |
| 116 | = VAR(A461:A464) | | | |
| 117 | = VAR(A465:A468) | | | |
| 118 | = VAR(A469:A472) | | | |
| 119 | = VAR(A473:A476) | | | |
| 120 | = VAR(A477:A480) | | | |
| 121 | = VAR(A481:A484) | | | |
| 122 | = VAR(A485:A488) | | | |
| 123 | = VAR(A489:A492) | | | |
| 124 | = VAR(A493:A496) | | | |
| 125 | = VAR(A497:A500) | | | |
| 126 | = VAR(A501:A504) | | | |
| 127 | = VAR(A505:A508) | | | |
| 128 | = VAR(A509:A512) | | | |
| 129 | 4 | 8 | 16 | 32 |
| 130 | = AVERAGE(C1:C128) | = AVERAGE(D1:D128) | = AVERAGE(E1:E128) | = AVERAGE(F1:F128) |
| 131 | = LN(C129) | = LN(D129) | = LN(E129) | = LN(F129) |
| 132 | = LN(C130) | = LN(D130) | = LN(E130) | = LN(F130) |
| 133 | = STDEV(C1:C128) | = STDEV(D1:D128) | = STDEV(E1:E128) | = STDEV(F1:F128) |
| 134 | | | | |
| 135 | | = LN(C130) | | |
| 136 | | = LN(D130) | | |
| 137 | | = LN(E130) | | |
| 138 | | = LN(F130) | | |
| 139 | | = LN(G130) | | |
| 140 | | = LN(H130) | | |
| 141 | | = LN(I130) | | |
| 142 | | = LN(J130) | | |

| | G | H | I | J |
|---|---|---|---|---|
| 1 | = VAR(A1:A64) | = VAR(A1:A128) | = VAR(A1:A256) | = VAR(A1:A512) |
| 2 | = VAR(A65:A128) | = VAR(A129:A256) | = VAR(A257:512) | |
| 3 | = VAR(A129:A192) | = VAR(A257:A384) | | |
| 4 | = VAR(A193:A256) | = VAR(A385:A512) | | |
| 5 | = VAR(A257:A320) | | | |
| 6 | = VAR(A321:A384) | | | |
| 7 | = VAR(A385:A448) | | | |
| 8 | = VAR(A449:A512) | | | |
| 9 | | | | |
| 10 | | | | |
| 11 | | | | |
| 12 | | | | |
| 13 | | | | |
| 14 | | | | |
| 15 | | | | |
| 16 | | | | |
| 17 | | | | |
| 18 | | | | |
| 19 | | | | |
| 20 | | | | |
| 21 | | | | |
| 22 | | | | |
| 23 | | | | |
| 24 | | | | |
| 25 | | | | |
| 26 | | | | |
| 27 | | | | |
| 28 | | | | |
| 29 | | | | |
| 30 | | | | |
| 31 | | | | |
| 32 | | | | |
| 33 | | | | |
| 34 | | | | |
| 35 | | | | |
| 36 | | | | |
| 37 | | | | |
| 38 | | | | |
| 39 | | | | |
| 40 | | | | |
| 41 | | | | |
| 42 | | | | |
| 43 | | | | |
| 44 | | | | |

APPENDIX III-continued

Variance Computation 45
46
47
48
49
50
51
52
53
54
55
56
57
58
59
60
61
62
63
64
65
66
67
68
69
70
71
72
73
74
75
76
77
78
79
80
81
82
83
84
85
86
87
88
89
90
91
92
93
94
95
96
97
98
99
100
101
102
103
104
105
106
107
108
109
110
111
112
113
114
115
116
117
118
119
120
121

APPENDIX III-continued

| | Variance Computation | | | |
|---|---|---|---|---|
| 122 | | | | |
| 123 | | | | |
| 124 | | | | |
| 125 | | | | |
| 126 | | | | |
| 127 | | | | |
| 128 | | | | |
| 129 | 64 | 128 | 256 | 512 |
| 130 | = AVERAGE(G1:G128) | = AVERAGE(H1:H128) | = AVERAGE(I1:I128) | = AVERAGE(J1:J128) |
| 131 | = LN(G129) | = LN(H129) | = LN(I129) | = LN(J129) |
| 132 | = LN(G130) | = LN(H130) | = LN(I130) | = LN(J130) |
| 133 | = STDEV(G1:G128) | = STDEV(H1:H128) | = STDEV(I1:I128) | = STDEV(J1:J128) |
| 134 | | | | |
| 135 | | | | |
| 136 | | | | |
| 137 | | | | |
| 138 | | | | |
| 139 | | | | |
| 140 | | | | |
| 141 | | | | |
| 142 | | | | |

*Raw data from lock-in amplifier 1.
**Raw data from lock-in amplifier 2.

REFERENCES

1. Roncari, D A K: In Clinical Medicine (Spittell J A Jr, Volpe R, eds) Harper and Row, Philadelphia, Vol 9, Ch 14: 1–57, 1986.
2. Angel A, Wincour J T, Roncari D A K: In Surgery for the Morbidly Obese Patient (Deitel M, ed) Lea & Pebiger, Philadelphia, Ch 2: 19–26, 1989.
3. Hubert H B: Annu Rev Public Health 7: 493–502, 1986.
4. Howard B V: J Lipid Res 28: 613–628.
5. Brunzell J D, Austin M A: N Engl J Med 320: 1273–1274, 1989.
6. Simopoulos A P: Annu Rev Public Health 7: 481–492, 1986.
7. Colditz G A: Am J Clin Nutr 55: 503S–507S, 1992.
8. Roncari D A K: Med Hypotheses 23:11–18, 1987.
9. Hamilton B S, Nakamura K, Roncari D A K: Biochem Cell Biol 70: 255–258, 1992.
10. Alberts B, Bray D, Lewis J, Raff M, Roberts K, Watson J D: In Molecular Biology of the Cell, Second Edition, Garland Publishing Inc, New York, 41–86, 1989.
11. Goodnight S H Jr, Harris W S, Connor W E, Illingworth R D: Arteriosclerosis 2: 87, 1982.
12. Stubbs C D: In Essays in Biochemistry (Campbell P N, Marshall R D, eds) Academic Press for The Biochemical Society, London, Vol 19, 1983.
13. Lynch D V, Thompson G A Jr: Trends Biochem Sci 9: 442, 1992.
14. Hoffman W, Restall C J: In Biomembrane Structure and Function (Champman D, ed) Verlag Chemie, Weinheim, 1984.
15. Rockwell W J, Ellingwood E H Jr, Trader D W: South Med J 76: 1407, 1983.
16. Sheterline P: In Mechanisms of Cell Motility: Molecular Aspect of Contractility, Academic Press, New York, 1983.
17. Healy I A, Roncari R A K: Proc Fifth Heritage Medical Research Days, Alberta Heritage Foundation for Medical Research, 52, 1985.
18. Healy I A, M.Sc. Thesis, University of Calgary, 1987.
19. Astrup A, Buemann B, Christensen N J, Toubro S, Thorbek G, Victor O J, Quaade F: Metabolism 41: 686–688, 1992.
20. Lo C-M, Keese C R, Giaever I: Exp Cell Res 204, 102–109, 1993.
21. Saxton W M, Hicks J, Goldstein L S B, Raff EC: Cell 64, 1093–1102, 1991.
22. Bligh E G, Dyer W J: Can J Biochem Physiol 37, 911, 1959.
23. Van R L R, Baylis C E, Roncari D A K: J Clin Invest 58, 699–704, 1976.
24. Kandel J, Bossy-Wetzel E, Radvanyl F, Klagsbrun M, Folkman J, Hanahan D: Cell 66, 1095–1104, 1991.
25. Keith A D: Comp Biochem Physiol 17, 1127–1136, 1966.
26. Hauner H, Entenmann G, Wabitsch M, Gaillard D, Ailhaud G, Negrel L, Pfeiffer EF: J Clin Invest 84, 1663–1670, 1989.
27. Ben-Ze'ev A: Electrophoresis 11, 191–200, 1990.
28. Fernandez J L R, Ben-Ze'ev A: Differentiation 42, 65–74, 1989.
29. Allen R D: Ann Rev Biophys Biophys Chem 14, 265–290, 1985.
30. Hayden J H, Allen R D, Goldman R D: Cell Motil 3, 1–19, 1983.
31. Hayden J H, Allen R D: J Cell Biol 99, 1785–1793, 1984.
32. Miyata Y, et al: Exp Cell Res 175, 286–297, 1988.
33. Giaever I, Keese C R: Proc Natl Acad Sci USA 81, 3761–3764, 1984.
34. Giaever I, Keese C R: Proc Natl Acad Sci USA 88, 7896–7900, 1991.

What is claimed is:

1. A method for screening a compound as a potential anti-obesity agent, the method comprising the steps of:
culturing cellular material in the presence of the compound; and
ascertaining whether the compound increases the level of micromotion of the
cellular material beyond a predetermined level, which predetermined level is at least as great as micromotion of the cellular material in the absence of the compound, whereby a said determined level of micromotion above the predetermined level indicates that the compound is a potential anti-obesity agent in mammals.

2. The method of claim 1 wherein said cellular material is mammalian.

3. The method of claim 2 wherein said mammalian cellular material comprises undifferentiated cells.

4. The method of claim 3 wherein said cells are preadipocytes.

5. The method of claim 4 wherein the preadipocytes are from humans.

6. The method of claim 1 wherein determining the level of micromotion of the cellular material includes following fluctuations in impedance of electrodes serving as cell substrata.

7. The method of claim 6 wherein the electrodes are gold film electrodes.

8. The method of claim 1 wherein the predetermined level of micromotion is equal to that of the cellular material cultured in the absence of the compound.

9. The method of claim 1, further comprising the step of determining the predetermined level by measuring the micromotion of the cellular in the absence of the compound prior to culturing the cellular material in the presence of the compound.

* * * * *